(12) United States Patent
Alfieri et al.

(10) Patent No.: US 7,935,145 B2
(45) Date of Patent: May 3, 2011

(54) ANNULOPLASTY RING FOR ISCHEMIC MITRAL VALVE INSUFFUCIENCY

(75) Inventors: Ottavio Alfieri, Brescia (IT); Alain F. Carpentier, Paris (FR); Francesco Maisano, Milan (IT); Patrick McCarthy, Chicago, IL (US); Alberto Redaelli, Milan (IT)

(73) Assignee: Edwards Lifesciences Corporation, Irvine, CA (US)

( * ) Notice: Subject to any disclaimer, the term of this patent is extended or adjusted under 35 U.S.C. 154(b) by 1153 days.

(21) Appl. No.: 10/882,031

(22) Filed: Jun. 30, 2004

(65) Prior Publication Data

US 2005/0131533 A1    Jun. 16, 2005

Related U.S. Application Data

(63) Continuation of application No. 10/678,338, filed on Oct. 3, 2003, now abandoned, which is a continuation-in-part of application No. 10/192,516, filed on Jul. 8, 2002, now Pat. No. 6,858,039, and a continuation-in-part of application No. 10/144,932, filed on May 15, 2002, now Pat. No. 6,726,717.

(30) Foreign Application Priority Data

May 17, 2001    (IT) .............................. MI2001A1012

(51) Int. Cl.
*A61F 2/24* (2006.01)
(52) U.S. Cl. ...................................... 623/2.36
(58) Field of Classification Search ......... 623/2.36–2.42
See application file for complete search history.

(56) References Cited

U.S. PATENT DOCUMENTS 3,656,185 A * 4/1972 Carpentier .................. 623/2.36
(Continued)

FOREIGN PATENT DOCUMENTS

EP    0 338 994    10/1989
(Continued)

OTHER PUBLICATIONS

International Search Report with a mailing date of Jun. 20, 2005.
(Continued)

*Primary Examiner* — David Isabella
*Assistant Examiner* — Ann Schillinger
(74) *Attorney, Agent, or Firm* — AnneMarie Kaiser, Esq.; Guy Cumberbatch, Esq.

(57) ABSTRACT

A remodeling mitral annuloplasty ring with a reduced anterior-to-posterior dimension to restore coaptation between the mitral leaflets in mitral valve insufficiency (IMVI). The ring has a generally oval shaped body with a major axis perpendicular to a minor axis, both perpendicular to a blood flow axis. An anterior section lies between anteriolateral and posteriomedial trigones, while a posterior section defines the remaining ring body and is divided into P1, P2, and P3 segments corresponding to the three scallops of the same nomenclature in the posterior leaflet of the mitral valve. The anterior-to-posterior dimension of the ring body is reduced from conventional rings; such as by providing, in atrial plan view, a pulled-in P3 segment. Viewed another way, the convexity of the P3 segment is less pronounced than the convexity of the P1 segment. In addition, the ring body may have a downwardly deflected portion in the posterior section, preferably within the P2 and P3 segments. The downwardly deflected portion may have an apex which is the lowest elevation of the ring body and may be offset with respect to the center of the downwardly deflected portion toward the P1 segment. A sewing cuff may have an enlarged radial dimension of between 5-10 cm, or only a portion of the sewing cuff may be enlarged.

40 Claims, 12 Drawing Sheets

U.S. PATENT DOCUMENTS

| | | | | | |
|---|---|---|---|---|---|
| 3,725,961 | A | * | 4/1973 | Magovern et al. | 623/2.4 |
| 4,042,979 | A | * | 8/1977 | Angell | 623/2.37 |
| 4,055,861 | A | * | 11/1977 | Carpentier et al. | 623/2.36 |
| 4,164,046 | A | * | 8/1979 | Cooley | 623/2.36 |
| 4,217,665 | A | * | 8/1980 | Bex et al. | 623/2.36 |
| 4,489,446 | A | | 12/1984 | Reed | |
| 4,535,483 | A | * | 8/1985 | Klawitter et al. | 623/2.4 |
| 4,917,698 | A | | 4/1990 | Carpentier | |
| 5,061,277 | A | * | 10/1991 | Carpentier et al. | 623/2.36 |
| 5,104,407 | A | * | 4/1992 | Lam et al. | 623/2.36 |
| 5,201,880 | A | * | 4/1993 | Wright et al. | 623/2.37 |
| 5,258,021 | A | * | 11/1993 | Duran | 623/2.36 |
| 5,306,296 | A | * | 4/1994 | Wright et al. | 623/2.37 |
| 5,376,112 | A | * | 12/1994 | Duran | 623/1.26 |
| 5,450,860 | A | | 9/1995 | O'Connor | |
| 5,496,336 | A | | 3/1996 | Cosgrove et al. | |
| 5,607,471 | A | * | 3/1997 | Seguin et al. | 623/2.36 |
| 5,716,417 | A | * | 2/1998 | Girard et al. | 623/2.38 |
| 5,776,189 | A | * | 7/1998 | Khalid | 623/1.26 |
| 5,824,065 | A | * | 10/1998 | Gross | 623/2.41 |
| 5,824,069 | A | | 10/1998 | Lemole | |
| 6,019,739 | A | | 2/2000 | Rhee et al. | |
| 6,024,918 | A | | 2/2000 | Hendriks et al. | |
| 6,045,576 | A | * | 4/2000 | Starr et al. | 623/2.41 |
| 6,102,945 | A | * | 8/2000 | Campbell | 623/2.37 |
| 6,143,024 | A | * | 11/2000 | Campbell et al. | 623/2.36 |
| 6,159,240 | A | | 12/2000 | Sparer et al. | |
| 6,183,512 | B1 | | 2/2001 | Howanec, Jr. et al. | |
| 6,187,040 | B1 | * | 2/2001 | Wright | 623/2.36 |
| 6,217,610 | B1 | * | 4/2001 | Carpentier et al. | 623/2.37 |
| 6,231,602 | B1 | * | 5/2001 | Carpentier et al. | 623/2.36 |
| 6,250,308 | B1 | * | 6/2001 | Cox | 128/898 |
| 6,258,122 | B1 | | 7/2001 | Tweden et al. | |
| 6,409,759 | B1 | * | 6/2002 | Peredo | 623/2.13 |
| 6,419,696 | B1 | * | 7/2002 | Ortiz et al. | 623/2.37 |
| 6,726,717 | B2 | | 4/2004 | Alfieri et al. | |
| 6,805,710 | B2 | | 10/2004 | Bolling et al. | |
| 6,858,039 | B2 | | 2/2005 | McCarthy | |
| 2001/0034551 | A1 | | 10/2001 | Cox | |
| 2001/0044656 | A1 | * | 11/2001 | Williamson et al. | 623/2.11 |
| 2002/0129820 | A1 | | 9/2002 | Ryan et al. | |
| 2002/0169504 | A1 | | 11/2002 | Alferness et al. | |
| 2002/0173844 | A1 | | 11/2002 | Alfieri et al. | |
| 2003/0033009 | A1 | * | 2/2003 | Gabbay | 623/2.36 |
| 2003/0040793 | A1 | | 2/2003 | Marquez | |
| 2003/0083742 | A1 | | 5/2003 | Spence et al. | |
| 2003/0093148 | A1 | * | 5/2003 | Bolling et al. | 623/2.36 |
| 2005/0004666 | A1 | | 1/2005 | Alfieri | |

FOREIGN PATENT DOCUMENTS

| | | |
|---|---|---|
| EP | 0 595 791 | 5/1994 |
| EP | 0 860 151 | 8/1998 |
| EP | 1 034 753 | 9/2000 |
| WO | WO 95/03757 | 2/1995 |
| WO | WO 01/19292 | 3/2001 |
| WO | WO 01/26586 | 4/2001 |
| WO | WO 01/87191 | 11/2001 |
| WO | WO 02/03892 | 1/2002 |

OTHER PUBLICATIONS

Edwards Lifesciences, Carpentier-Edwards Classic Mitral Annuloplasty Ring, www.ctsnet.org/Edwards/product/702.

Seguin, et al., Advance in Mitral Valve Repair Using a Device Flexible in Three Dimensions, The St Jude Medical-Seguin Annuloplasty Ring, ASAIO Journal, vol. 42, No. 6, pp. 368-371, 1996.

D.C. Miller, IMR Redux—To Repair or Replace?, Journal of Thoracic & Cardiovascular Surgery, pp. 1-8, 2001.

Richard P. Cochran, et al., Effect of Papillary Muscle Position on Mitral Valve Function: Relationship to Homografts, The Society of Thoracic Surgeons, pp. 5155-5161, 1998.

Melo, J. Q., et al., Atrioventricular Valve Repair Using Externally Adjustable Flexible Rings, The Journal of Thoracic and Cardiovascular Surgery, pp. 1333-1337, vol. 110, No. 5, Nov. 1995.

Alonso-Lei, Adjustable Annuloplasty for Tricuspid Insufficiency, The Annals of Thoracic Surgery, pp. 368-369, vol. 46, No. 3, Sep. 1988.

Giuseppe Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Salgo, et al., Effect of Annular Shape on Leaflet Curvature in Reducing Mitral Leaflet, American Heart Association, Circulation 200; pp. 106-711.

MGH Study Shows Mitral Valve Prolapse Not a Stroke Risk Factor, Massachusetts General Hospital, pp. 1-3, Jun. 1999.

Techniques for 3D Quantitative Echocardiography, University of Washington Cardiovascular Research & Training Center Cardiac Imaging Research Lab, pp. 1-5, Oct. 2003.

Bolling, Mitral Valve Reconstruction in the Patient With Heart Failure, Heart Failure Reviews, 6, pp. 177-185, 2001.

Bolling, et al., Surgical Alternatives for Heart Failure, The Journal of Heart and Lung Transplantation, vol. 20, No. 7, pp. 729-733, 2001.

Smolens, et al., Mitral Valve Repair in Heart Failure, The European Journal of Heart Failure 2, pp. 365-371, 2000.

Carpentier-Edwards CLassic Annuloplasty Ring with Duraflo Treatment Models 4425 and 4525 for Mitral and Tricuspid Valvuloplasty, Baxter Healthcare Corporation, 1998.

The "Physio-Ring": An Advanced Concept in Mitral Valve Annuloplasty, Carpentier, et al., Ann Thorac Surg 1995;60:1177-1185.

Three-dimensional geometric comparison of partial and complete flexible mitral annuloplasty rings, Dagum, et al., Surg for Acquired Cardiovascular Disease 2001; 122, 4: 665-673.

PHYSIO Annuloplasty Ring Elgiloy Band Engineering Drawing, Edwards Lifesciences, 1995.

* cited by examiner

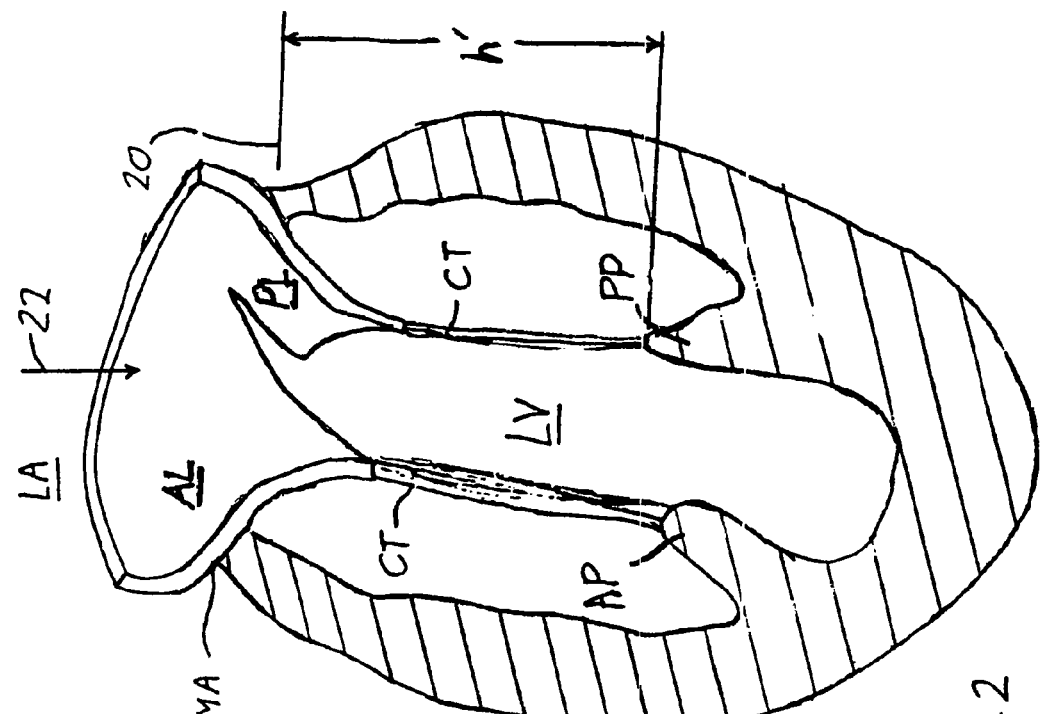
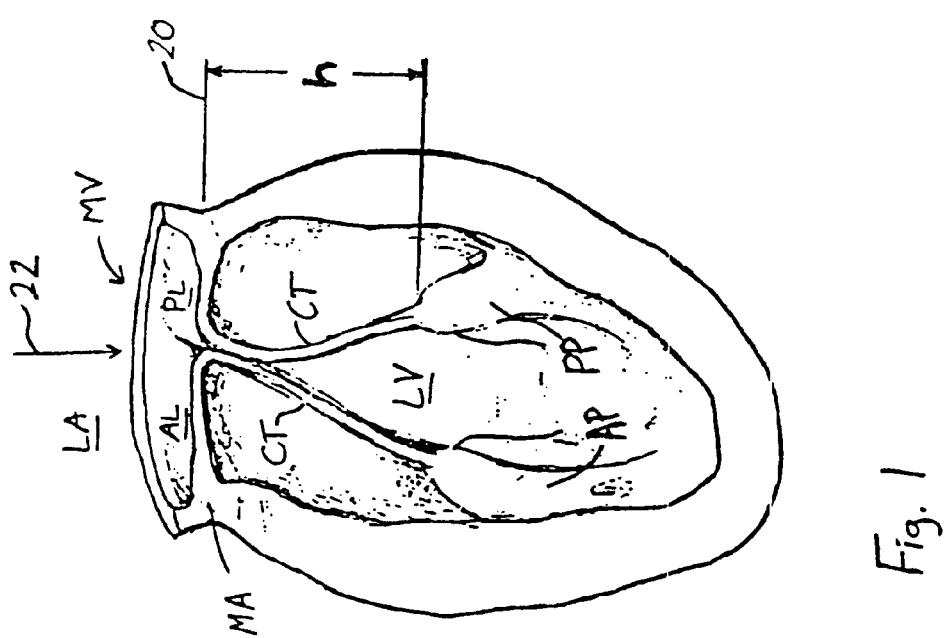
Fig. 2
Fig. 1

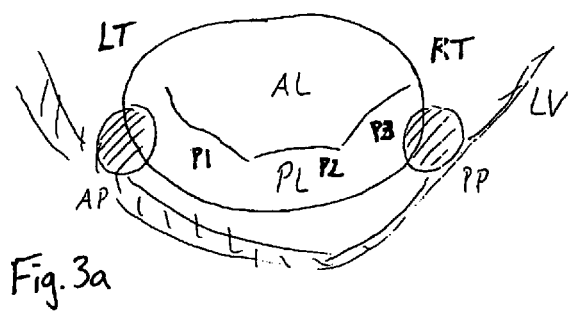
Fig. 3a
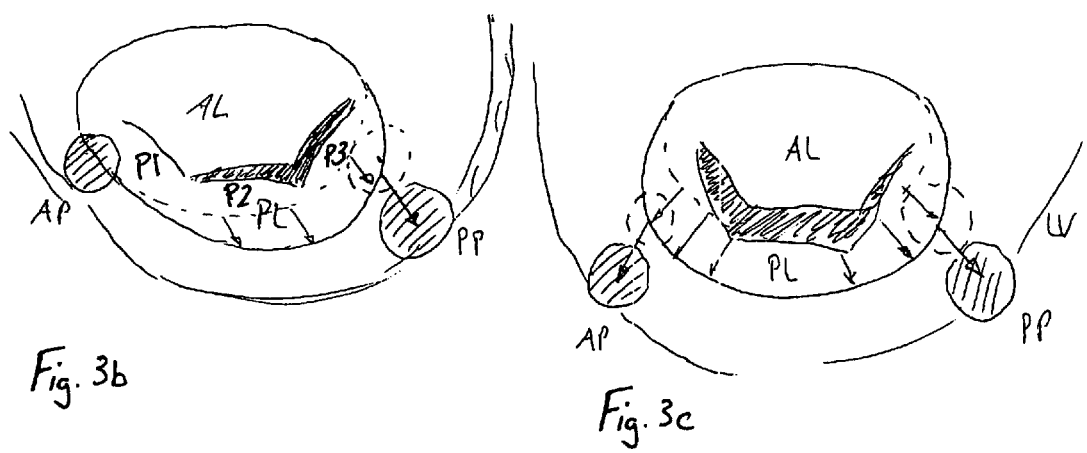
Fig. 3b
Fig. 3c

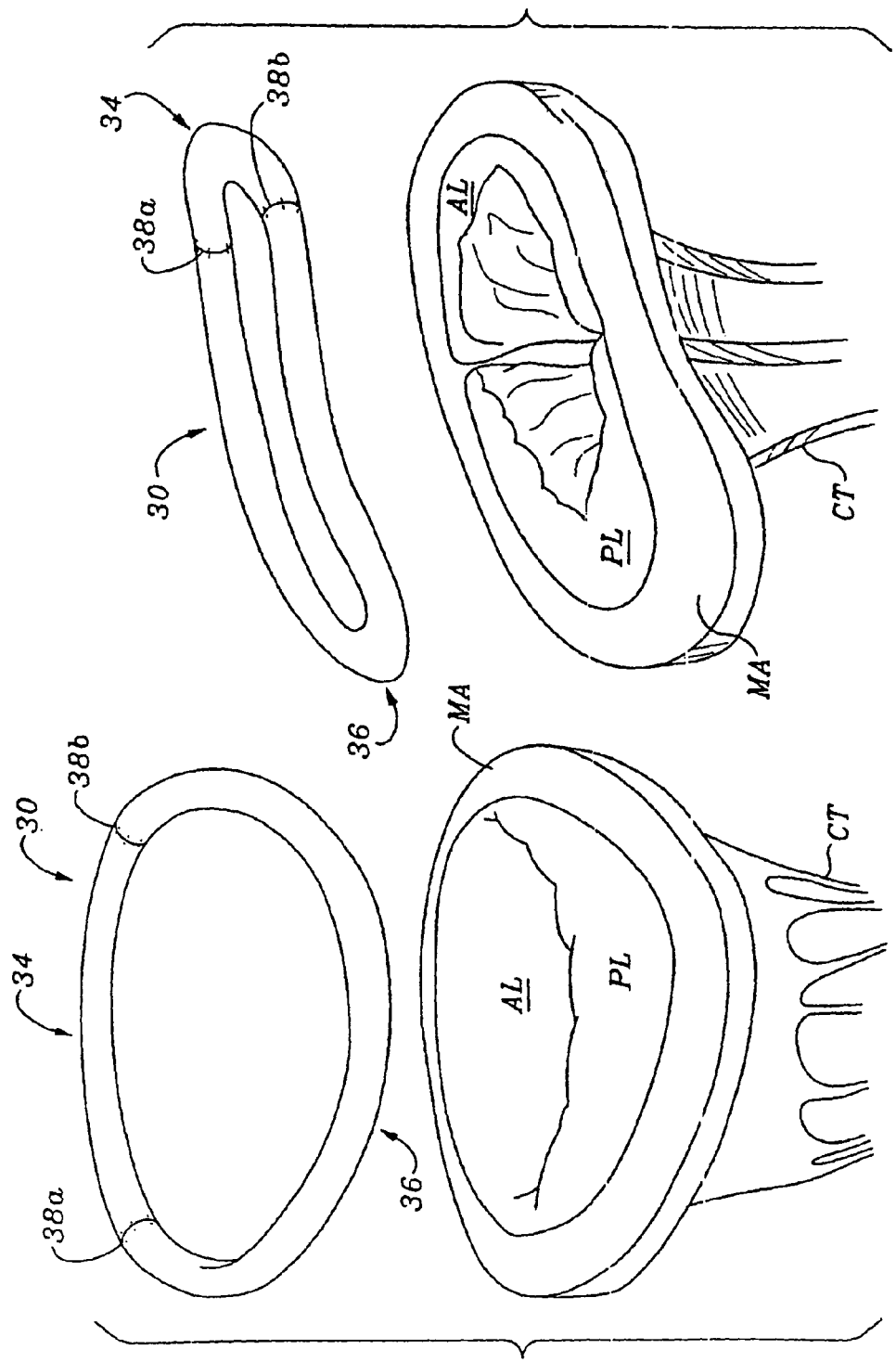

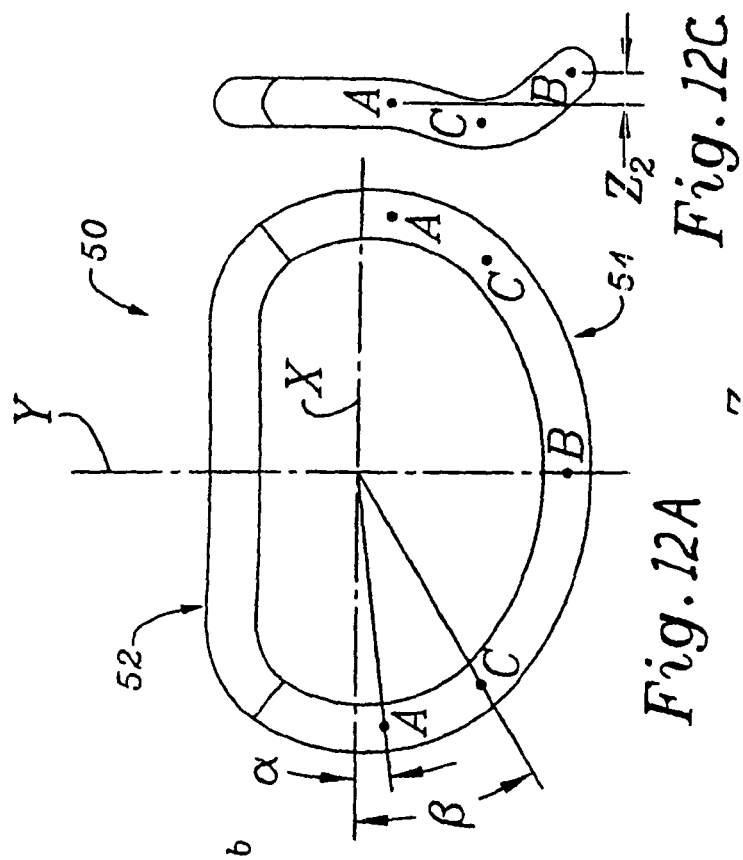
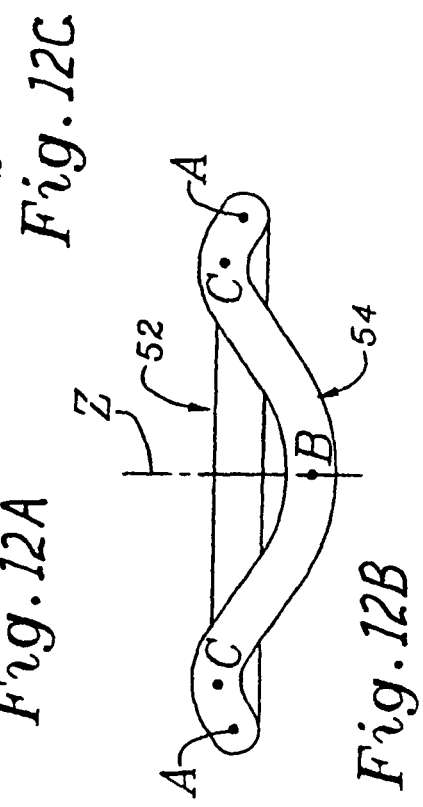
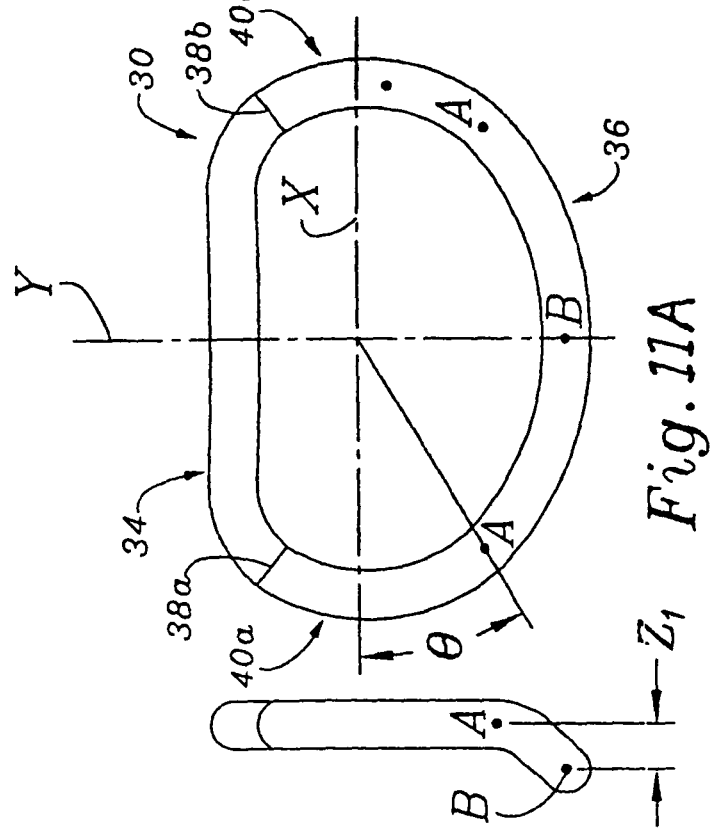
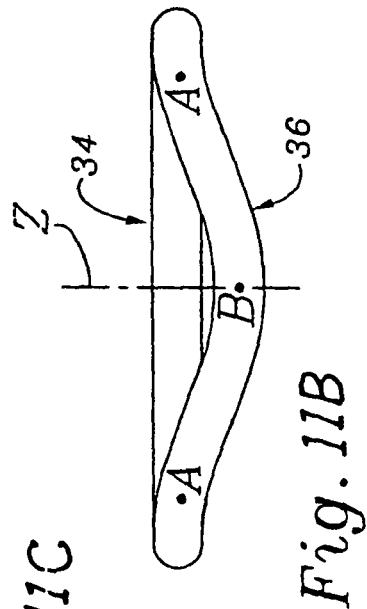
Fig. 11A  Fig. 11B  Fig. 11C  Fig. 12A  Fig. 12B  Fig. 12C

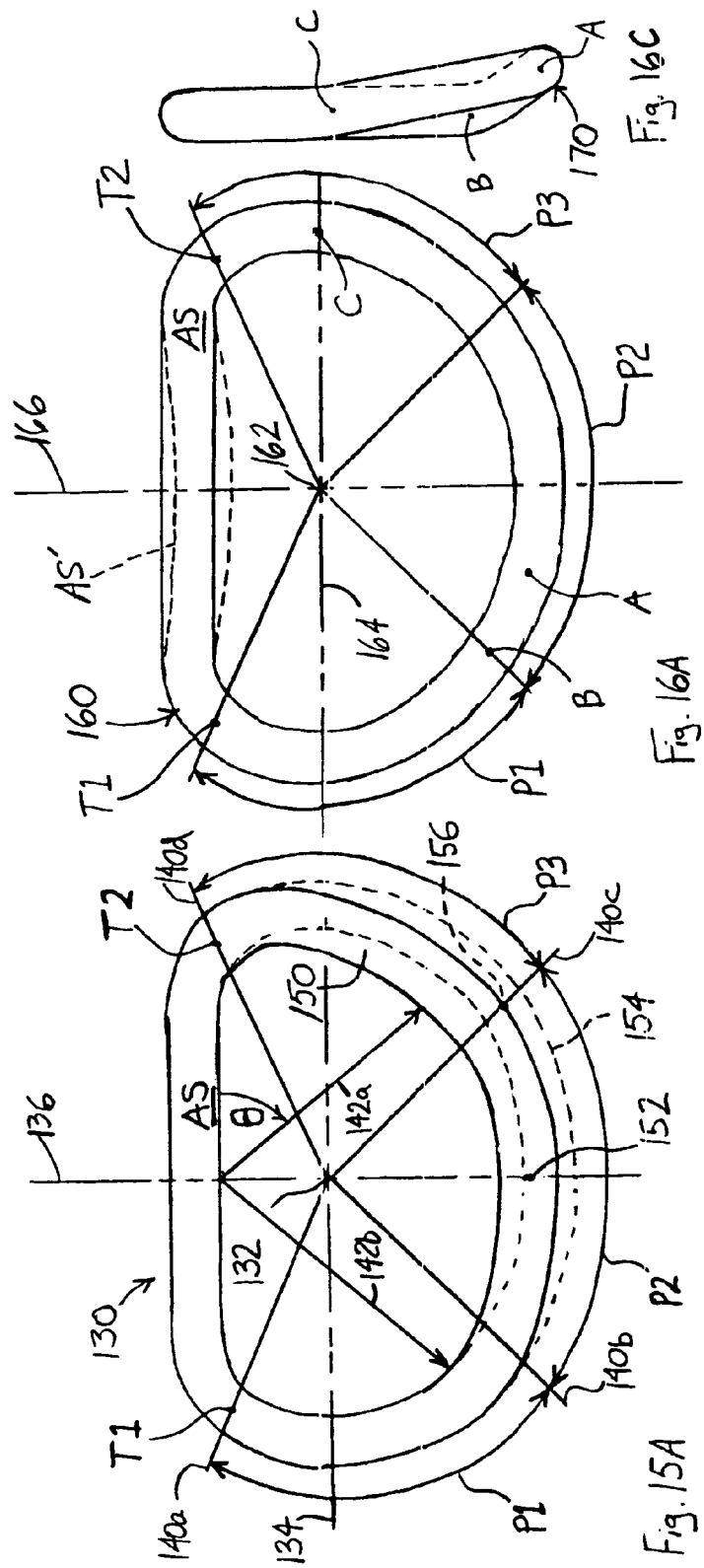
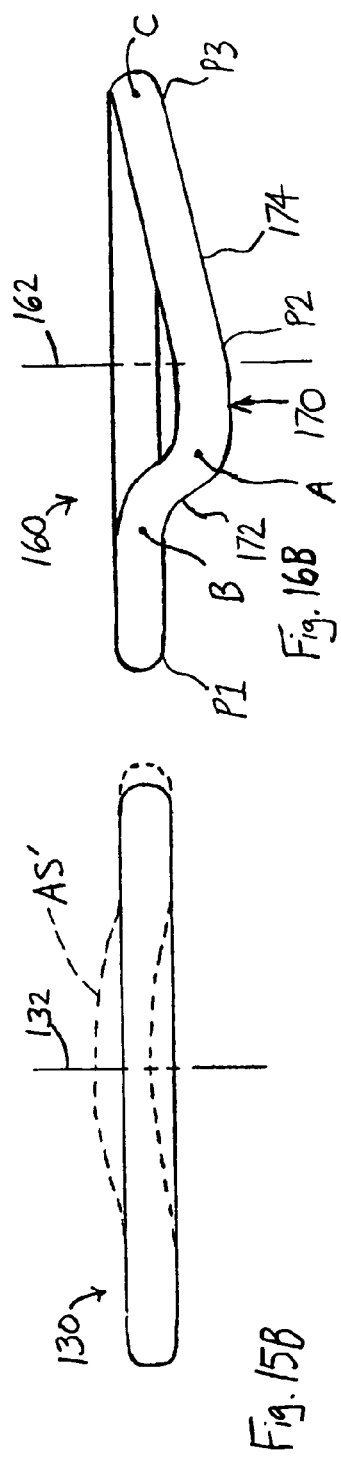

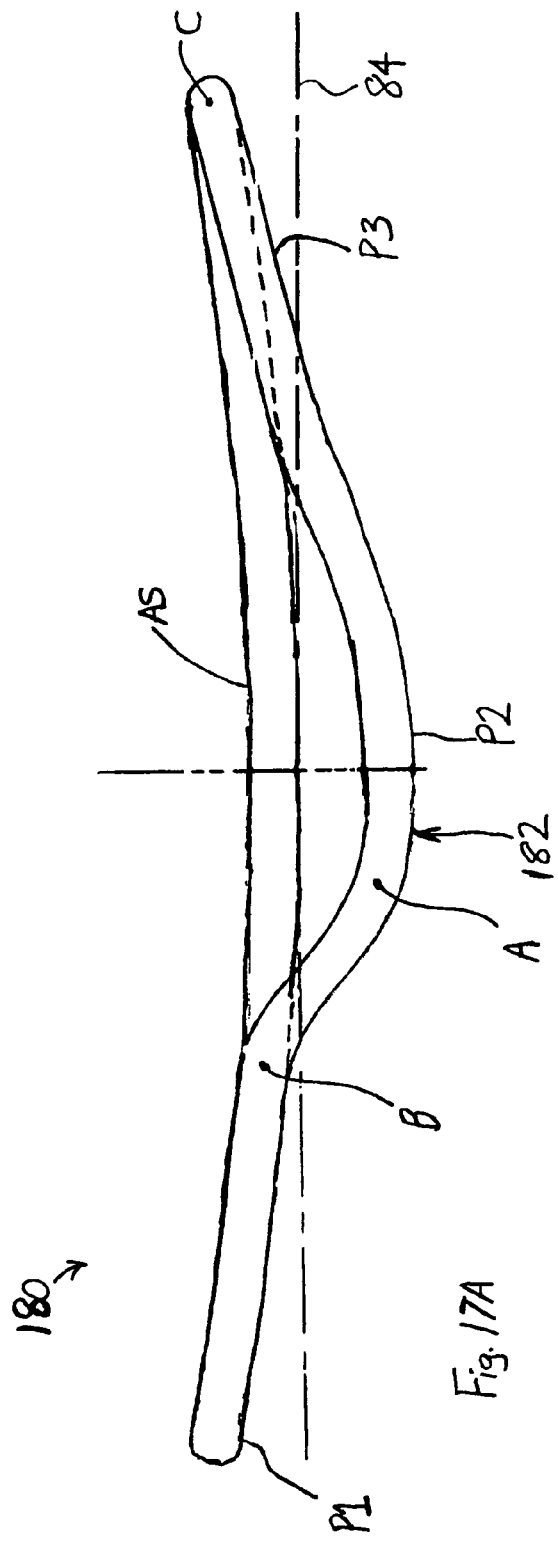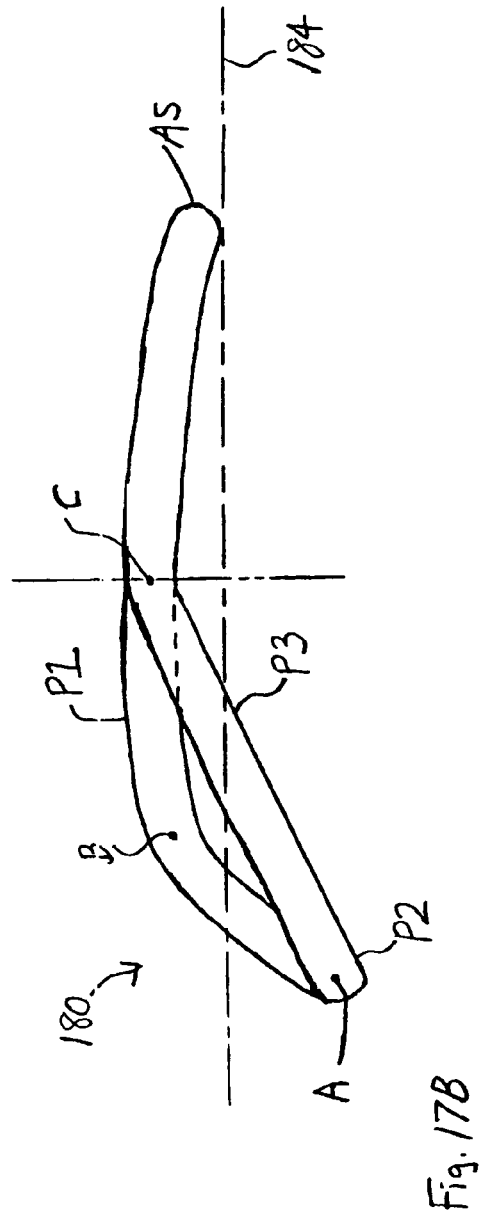

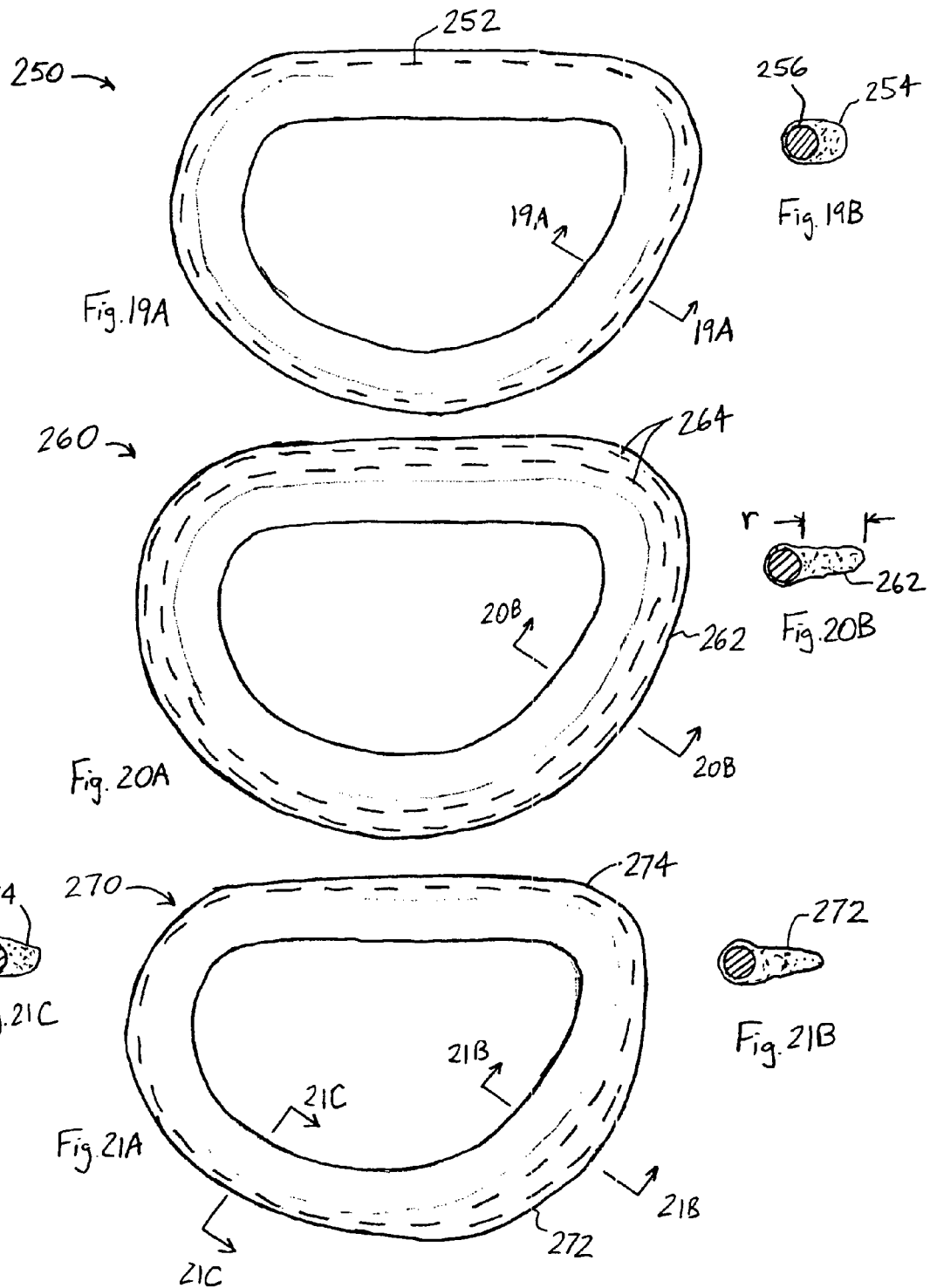

ANNULOPLASTY RING FOR ISCHEMIC MITRAL VALVE INSUFFUCIENCY

RELATED APPLICATIONS

The present application is a continuation of U.S. application Ser. No. 10/678,338, filed Oct. 3, 2003, now abandoned which is a continuation-in-part to U.S. application Ser. No. 10/192,516, filed Jul. 8, 2002, now U.S. Pat. No. 6,858,039 entitled "Mitral Valve Annuloplasty Ring Having a Posterior Bow." The present application is also a continuation-in-part to U.S. application Ser. No. 10/144,932, filed May 15, 2002, now U.S. Pat. No. 6,726,717 entitled "Annular Prosthesis for Mitral Valve," which claims priority under 35 U.S.C. §119 to Italian Application No. MI 2001A 001012, filed May 17, 2001.

FIELD OF THE INVENTION

The present invention relates generally to medical devices, specifically to an annuloplasty ring and related procedure for surgically reconstructing the mitral valve annulus of a patient's heart. More specifically, this invention relates to a mitral valve annuloplasty ring and corresponding technique designed to correct an abnormal annulus in the pathology encountered with all functional anomalies seen with ischemic mitral valve insufficiency (IMVI), or other pathologies resulting in functional mitral regurgitation.

BACKGROUND OF THE INVENTION

In the anatomy of the human heart, the left atrium receives oxygenated blood from the lungs through the pulmonary veins. The mitral valve separates the left atrium from the left ventricle. During diastole, as the contraction triggered by the sinoatrial node progresses through the atria, oxygenated blood passes through the mitral valve into the left ventricle. In this phase, the aortic valve leading into the ascending aorta closes, allowing the left ventricle to fill with blood. A similar flow of venous blood occurs from the right atrium through the tricuspid valve to the right ventricle. Once the ventricles are full, they contract during the systolic phase and pump blood out of the heart. During systole, the mitral valve closes and the aortic valve opens, thus preventing blood from regurgitating into the left atrium and forcing blood into the aorta, and from there throughout the body. Because of the high pressures associated with the left ventricle during systole, proper functioning of the mitral valve to prevent blood from flowing back through the system is extremely important.

The various anatomical components of a healthy mitral valve are depicted in FIG. 1. The mitral annulus MA comprises a fibrous ring encircling the orifice between the left atrium LA and the left ventricle LV. The average cross-sectional area of the human mitral annulus is 4-10 cm². The mitral valve is a bicuspid valve having a posterior leaflet PL and an anterior leaflet AL. Chordae tendenae CT (or simply "chordae") extend from the free edges and the bases of the two leaflets to a pair of papillary muscles located in the LV. The two papillary muscles are located along the anteriolateral and the posteromedial wall of the LV and are therefore referred to as the anteriolateral papillary muscle AP and the posteromedial papillary muscle PP, respectively.

Normal dilatation of the left ventricle and downward displacement of the papillary muscles AP and PP pulls the chordae tendoneae CT, which in turn pull the leaflets open. When the ventricles contract the papillary muscles are displaced upward, and the distance h between the papillary muscles and the annulus is reduced. The chordae tendonae become slack, allowing the leaflets to come together or "coapt." As seen in FIG. 1, the leaflets coapt along a substantial surface area in the normal functioning heart, with the free edges of the leaflets mutually bending toward the left ventricle LV. For purpose of discussion, the mitral annulus MA of a normal, healthy heart lies generally in a datum plane 20 defined perpendicular to the average blood flow direction 22 through the mitral valve MV. Although a typical mitral annulus MA may be three-dimensional, the datum plane 20 is representative of the relative positions of the anterior and posterior side of the annulus.

In patients who suffer from a heart attack or cardiomyopathy, regions of the left ventricle lose their contractility and dilate. Dilation of the left ventricle is often associated with a down and outward displacement of the papillary muscles. The change in the location of the papillary muscles increases the distance between the papillary muscles and the mitral valve leaflets. Since the chordae tendenae do not change their length significantly, the chordae tend to pull or "tether" the leaflets. In severe cases of left ventricle dilatation, the tethering of the chordae prevents the leaflets from coapting resulting in mitral regurgitation. Since this type of regurgitation is not associated with any disease or damage of the mitral apparatus it is often referred to as "functional" mitral regurgitation. Dilation of the left ventricle LV is also a symptom associated with mitral regurgitation in patients with iopathic dilated cardiomyopathy or ischemic cardiomyopathy, and in patients with long-standing valvular regurgitation from other etiologies such as myxomatous disease, endocarditis, congenital defects, or rheumatic valvular disease.

As seen in FIG. 2, dilation of the left ventricle LV generally increases the distance h' between the papillary muscles $PM_1$ and $PM_2$ and the mitral annulus MA. The increased distance h' between the papillary muscles $PM_1$ and $PM_2$ and the mitral annulus MA in turn increases the tension in the chordae tendonae CT and may create a depression of the posterior aspect of the annulus below the datum plane 20, but this depression is not pronounced enough to reduce h'. The resulting increased tension in the chordae reduces the ability of the leaflets to come together during systole, which can lead to mitral valve insufficiency.

FIGS. 3a-3c illustrate the normal and abnormal mitral valve from the left atrium as exposed during surgery, that is, in atrial plan view. The anterior aspect of the mitral annulus MA forms a part of the "cardiac skeleton" and includes left and right fibrous trigones, LT and RT. The left trigone LT and right trigone RT are indicated at the junction points of the anterior leaflet AL and posterior leaflet PL. These junction points are also known as anteriolateral and posteriomedial trigones or commissures between the leaflets. The posterior aspect of the mitral annulus MA, in contrast to the anterior aspect, consists mainly of muscular tissue of the outer wall of the heart. The posterior leaflet PL is divided into three scallops indicated as P1, P2, and P3 in sequence from the left trigone LT counterclockwise to the right trigone RT. FIG. 3a shows the mitral valve and the papillary muscles of a normal mitral valve viewed from the left atrium. FIG. 3b illustrates the effect of an infarct of the posteromedial wall of the left ventricle LV on the geometry of the mitral apparatus, tending to cause an asymmetric dilation. The infarct causes the posteriomedial wall to dilate moving the posteromedial papillary muscle PP outward. The chordae tendenae CT connected to the posteromedial papillary muscle PP pull the free margins of the posterior leaflet PL and anterior leaflet AL away from the natural line of coaptation. A gap is created between the leaflets along the P2-P3 region of the posterior leaflet PL.

Asymmetric dilatation of the left ventricle LV associated with a regurgitating jet in the P2-P3 region is most common in patients with ischemic mitral regurgitation. In contrast, FIG. 3c illustrates functional mitral regurgitation in the case of symmetrical dilatation of the LV. Both papillary muscles AP and PP move outward, stretching and pulling the whole posterior leaflet PL outward. Symmetrical dilatation of the LV is associated with dilatation of the posterior segment of the mitral annulus and a central regurgitant jet along the P2 region of the PL. Symmetrical dilatation of the LV is most common in patients with cardiomyopathy.

Mitral valve insufficiency is commonly treated by repairing or replacing the mitral valve. The most widely accepted technique for mitral valve repair is the remodeling of the mitral annulus with an annuloplasty. The goal of the annuloplasty is two-fold: reduction of the annular area to its normal size and reshaping of the annulus to re-establish the normal geometry of a health mitral annulus. In case of functional mitral regurgitation, the root cause of the insufficiency is the dilation of the LV and the associated dislocation of the papillary muscle. The purpose of the annuloplasty is to compensate for the dilation of the LV by reducing the cross-sectional area beyond its natural size. The downsized annulus brings the two leaflets closer together re-establishing coaptation of the leaflets.

Prostheses for annuloplastic surgery available on the market are generally of two types, with some hybrids. Flexible annular prostheses, made of various materials, that allow a "linear" reduction of the annular circumference, and rigid and semi-rigid annular prostheses made of various materials, that allow the "linear" reduction of the annular circumference and a geometric remodelling so as to re-establish the physiological systolic shape of the annulus. Additionally, semi-rigid prostheses permit some deformation in order to allow the prosthesis to follow the deformations of the annulus—during the cardiac stages. All the rigid and semi-rigid annular prostheses have a kidney-like or coupled D shape, with an anterior half-ring, rectilinear in first approximation, that gets sutured in correspondence with the anterior valve leaflet and a curved posterior half-ring that is sutured in correspondence with the posterior valve leaflet. The shape of the annular prostheses at issue reproduces the configuration of the valve annulus during the ventricular systole, and therefore in the stage of the valve closing. The ratio between minor axis and major axis is approximately 3:4 in all the models currently on the market since it reproduces normal anatomical ratios.

The "downsizing" technique involves, for example, selecting a 26 mm ring for a nominal 28 mm annulus, while still maintaining the minor axis/major axis size ratio of approximately 3:4. The size nomenclature refers to the width of the major axis. Although good results have been reported with the downsizing technique, the reliability and durability of this operation to correct ischemic mitral valve insufficiency are not as good as for other causes of mitral valve insufficiency using the same techniques. This is largely due to the fact that a remodeling annuloplasty with currently available rings corrects only one anomaly, and various other functional anomalies seen in ischemic mitral valve insufficiency may not be corrected as effectively.

Annuloplasty rings have been developed in various shapes and configurations over the years to correct mitral regurgitation and other conditions that reduce the functioning of the valve. For example, Carpentier, et al. in U.S. Pat. No. 4,055,861 disclosed two semi-rigid supports for heart valves, one of which being closed (or D-shaped) and the other being open (or C-shaped). In the closed configuration, the ring is generally symmetric about an anterior-posterior plane, and has a convex posterior side and a generally straight anterior side. U.S. Pat. Nos. 5,104,407, 5,201,880, and 5,607,471 all disclose closed annuloplasty rings that are bowed slightly upward on their anterior side. Because the anterior aspect of the mitral annulus MA is fibrous and thus relatively inflexible (at least in comparison to the posterior aspect), the upward curve in the anterior side of each ring conforms that ring more closely to the anatomical contour of the mitral annulus. This three dimensional configuration reduces undue deformation of the annulus.

In general, conventional annuloplasty rings are intended to restore the original configuration of the mitral annulus MA. When correcting a condition as seen in FIG. 2, high stresses are created in the sutures connecting the annuloplasty ring to posterior aspect of the annulus because the "overcorrecting ring," i.e., a ring 1 to 2 sizes smaller than the normal size "pulls" the annulus inward and upward. The stresses sometimes result in the dehiscence or separation of the ring from the annulus because the sutures pull through the tissue.

It should be noted here that correction of the aortic annulus requires a much different ring then with a mitral annulus. For example, U.S. Pat. Nos. 5,258,021 and 6,231,602 disclose sinusoidal or so-called "scalloped" annuloplasty rings that follow the up-and-down shape of the three cusp aortic annulus. Such rings would not be suitable for correcting a mitral valve deficiency.

While good results in the treatment of mitral valve insufficiency, congestive heart failure, and mitral regurgitation have been obtained in the preliminary applications of the above-described methods and apparatuses, it is believed that these results can be significantly improved. Specifically, it would be desirable to produce a mitral annuloplasty ring that takes into consideration all of the dysfunctions that exist in ischemic mitral valve insufficiency, namely, the dilatation of the annulus, the asymmetrical deformation of the annulus, and the increased distance between the posterior papillary muscle and the annulus.

SUMMARY OF THE INVENTION

The inventors have noticed that in certain pathological conditions, there is a need to modify the minor axis/major axis size ratio in order to make the operation of reconstruction of the mitral valve more effective: for instance in order to bring the valve leaflets closer to each other in the case of anatomical or functional tissue deficiency of one or both leaflets. It has also been observed that anatomical variations that do not correspond to the conventionally accepted ratio of 3:4 are frequent in nature.

According to present the invention, better mitral annulus repair results have been attained by means of an annular prosthesis made up of a posterior half-ring and an anterior half-ring that are coupled to each other on a first transverse plane which defines a maximum width section of the prosthesis, characterised in that the ratio between the distance between said anterior half-ring and said posterior half-ring, as measured along a second plane, perpendicular to said first plane and equidistant to said couplings, and said maximum width of the prosthesis is lower than 3:4.

In one aspect, the present invention provides an annuloplasty ring for implantation in a mitral valve annulus that has a pathologic condition such that the posterior aspect thereof droops downward abnormally. The annuloplasty ring includes a rounded ring body having an anterior section and a posterior section. The ring body is oriented about a central flow axis that defines an upward direction and a downward direction, the downward direction corresponding to the direction of blood flow through the mitral valve annulus. The posterior section the ring body bows downward out of a plane perpendicular to the central flow axis.

The ring body may bow downward between about 2-15 mm from one end thereof to a lowest point, and desirably bows downward between about 4-8 mm from one end thereof to a lowest point. The bow in the ring body may or may not be centered in the posterior section, and in certain cases of ischemic mitral valve insufficiency is centered in the P3 segment of the ring. Preferably, the ring body is made of a malleable material such that the bow in the ring body may be manually reshaped. Desirably, the ring body is made of a semi-rigid material that will retain its posterior bow in opposition to the stresses that will be imparted by muscles of the heart throughout each beating cycle. The ring body may be substantially planar except in the posterior section, or an anterior section of the ring body may bow upward from one end thereof to a lowest point.

In plan view, as seen along the flow axis, the ring body preferably defines an oval shape with a major axis perpendicular to a minor axis, the minor axis bisecting both the anterior and posterior sections. Further, the bow in the posterior section may begin at symmetric locations across the minor axis that are spaced from the major axis around the ring body by an angle $\theta$ of between about 0-45°, more preferably about 30°.

The ring body may further include two upward bows on either side of the downward bow on the posterior section, and wherein downward bow may be between about 2-15 mm. In one embodiment, the ring body comprises a plurality of ring elements concentrically disposed. A polymer strip in between each ring element may be provided. Optionally, the ring elements comprise bands that have a substantially larger height in the flow axis dimension than in the dimension perpendicular to the flow axis. Further, the ring elements may have varying heights so that the ring body is more flexible in the posterior section than around the remainder of the ring body.

Another aspect of the present invention is a method of repairing a mitral heart valve annulus that has a posterior aspect that is depressed downward along the blood flow axis relative to an anterior aspect. The method includes implanting an annuloplasty ring having an anterior section sized to fit the anterior aspect of the annulus and a posterior section sized to the posterior aspect, wherein the ring posterior section bows downward parallel to the central axis relative to the anterior section. The annuloplasty ring may be malleable and the surgeon adjusts the bow in the posterior section manually.

Another aspect of the invention is a method of repairing a mitral heart valve annulus that has a posterior aspect, an anterior aspect, and a blood flow axis. The method includes inspecting the shape of the mitral annulus and selecting a three-dimensional annuloplasty ring based on the shape of the mitral annulus. The selected annuloplasty ring has an anterior section and a posterior section generally arranged around a central axis. The central axis defines an upward direction and a downward direction, wherein the ring posterior section bows downward out of a plane perpendicular to the central axis. The method includes implanting the annuloplasty ring so that the ring posterior section attaches to the posterior aspect of the mitral valve annulus and the posterior section bows in the blood flow direction.

In a still further aspect, the present invention provides an annuloplasty ring for implantation in a mitral valve annulus that includes a rounded ring body having an anterior section and a posterior section. The ring body is oriented about a central flow axis that defines an upward direction and a downward direction, the downward direction corresponding to the direction of blood flow through the mitral valve annulus. The shape and dimension of the ring differs from the shape and dimension of the currently available rings in order to correct the three causes of valve dysfunction described above: 1) the ventricular diameter is reduced, 2) the ring is asymmetrical with inward advancement of the PC-P3 region creating a decrease in the oblique distance from there to the anterior side, and 3) the P2 and P3 regions of the ring are deflected downward in order to reduce the increased distance h' between the annulus and the posterior papillary muscle.

In accordance with one particular aspect of the invention, an annuloplasty ring for implantation in a mitral valve annulus is provided that is designed to correct ischemic mitral valve insufficiency. The annuloplasty ring comprises a generally oval shaped ring body oriented about a central flow axis that defines an upward direction and a downward direction. The downward direction corresponds to the direction of blood flow through the mitral valve annulus from the left atrium to the left ventricle. In plan view, as seen along the flow axis, the ring body has a major axis perpendicular to a minor axis, the major and minor axes being perpendicular to the flow axis. In atrial plan view the ring body has an anterior section generally defined between an anterolateral trigone and a posteromedial trigone, and a posterior section around the remaining periphery of the ring body and between trigones. The posterior section is divided into three sequential segments, P1, P2, and P3, starting from the anterolateral trigone and continuing in a counterclockwise direction, wherein the minor axis intersects both the anterior section and the P2 segment of the posterior section.

In one version of the ring designed to correct ischemic mitral valve insufficiency, given a predetermined major axis dimension, the ratio of the minor axis dimension to the major axis dimension is less than 3:4 by reducing the absolute value of the minor axis dimension by between about 2-4 mm from an exact 3:4 ratio so as to restore the coaptation between the two leaflets without reducing excessively the overall orifice area of the annuloplasty ring.

In another version of the ring designed to correct ischemic mitral valve insufficiency, the ring body lies substantially in a plane defined by the major and minor axes or in a saddle-shaped three-dimensional surface except for a portion of the posterior section located within the P2 and P3 segments which is deflected downward with respect to the remaining sections of the ring body. The downwardly deflected portion includes an apex which is the lowest elevation of the ring body, and wherein the apex is off-center in the downwardly deflected portion toward the P1 segment of the ring body. As a result, in a posterior elevational view, a transition of the ring body between the P1 segment and the apex extends along a shorter distance around the ring body than a transition of the ring body between the apex and the non-downwardly-deflected portion of the P3 segment.

Any of the annuloplasty rings of the present invention may further include a sewing cuff around the ring body having an enlarged portion around the periphery of the ring body that can accommodate two radially adjacent rows of suture lines. Markings are desirably provided on the sewing cuff to indicate placement of the two radially adjacent rows of suture lines. The enlarged portion of the sewing cuff may extend around less than the entire periphery of the ring, and is preferably at least partly in the P3 segment.

BRIEF DESCRIPTION OF THE DRAWINGS

FIG. 1 is a cross-section of a healthy left ventricle through the mitral valve between the anterior and posterior leaflets;

FIG. 2 is a cross-section of a dilated left ventricle through the mitral valve between the anterior and posterior leaflets;

FIGS. 3a-3c illustrate normal and abnormal mitral valves from the left atrium as exposed during surgery, that is, in atrial plan view;

FIG. 9 is a perspective view of an annuloplasty ring of the present invention over an abnormal mitral valve as viewed from the posterior side;

FIG. 10 is a perspective view of the annuloplasty ring of FIG. 9 over the abnormal mitral valve as seen from the side;

FIGS. 11A-11C are plan, front, and side views of an exemplary annuloplasty ring of the present invention having a posterior bow;

FIGS. 12A-12C are plan, front, and side views of an alternative annuloplasty ring of the present invention having a posterior bow between two raised portions;

FIGS. 15A and 15B are atrial plan and posterior elevational views, respectively, of a generally planar exemplary annuloplasty ring of the present invention having an asymmetric configuration about a minor axis so as to have a reduced anterior-posterior dimension;

FIGS. 16A, 16B, and 16C are atrial plan, posterior elevational, and medial elevational views, respectively, of a further exemplary annuloplasty ring of the present invention having a downwardly deflected posterior portion;

FIGS. 17A and 17B are posterior elevational and medial elevational views, respectively, of a saddle-shaped annuloplasty ring of the present invention having a downwardly deflected posterior portion;

FIGS. 19A and 19B are atrial plan and sectional views of an annuloplasty ring of the present invention showing a standard sewing cuff;

FIGS. 20A and 20B are atrial plan and sectional views of an annuloplasty ring of the present invention showing a modified sewing cuff radially enlarged around the entire ring periphery; and FIGS. 21A-21C are atrial plan and sectional views of an annuloplasty ring of the present invention showing a modified sewing cuff with a radially enlarged segment.

DESCRIPTION OF THE PREFERRED EMBODIMENTS

Figure 4:
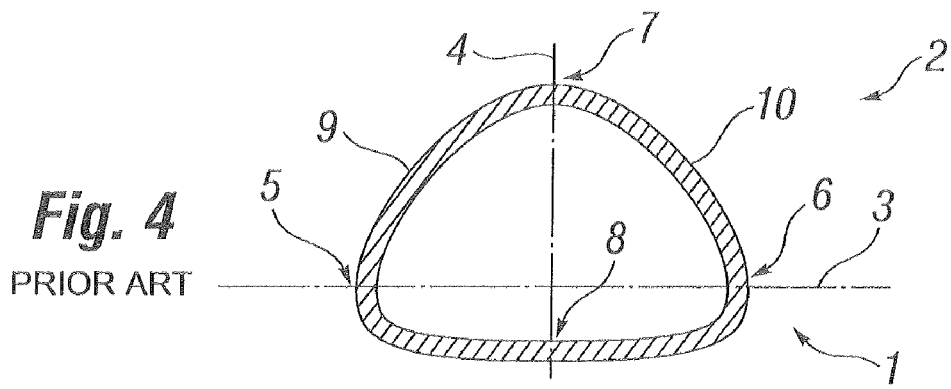
FIG. 4 shows an annular prosthesis for the mitral valve according to the known art.

The present invention provides various annuloplasty rings for correcting all the dysfunctions that exist in ischemic mitral valve insufficiency, and other pathologies not adequately corrected by prosthetic rings of the prior art. Various embodiments are shown and described in the present application with features that can be utilized independently or in combination. It should be understood, therefore, that any of the features described herein can be supplemented by one or more of the other features. Indeed, a particularly useful combination is believed to be either a reduction in the anterior-posterior dimension or a "pulled-in" P3 segment, in conjunction with a downward bow in the posterior section.

The attached figures illustrate several exemplary embodiments of the annuloplasty ring of the present invention, which can be described as being continuous and having an anterior section, a posterior section and right and left sides. All of the sides are generally curvilinear with no specific demarcations to indicate abrupt transitions therebetween. Rather, smooth transitional sections between the adjacent sides provide curvilinear connections that give the ring a generally rounded (e.g., oval) configuration.

The annuloplasty rings of the present invention are described as generally having an oval shape. This definition is intended to encompass various shapes in atrial plan view that are continuous around a periphery and are longer in one dimension (along a major axis) than in a perpendicular direction (along a minor axis). As seen from the figures, the shapes are not precisely ovals but are more similar to a capital "D", or can be likened to a kidney bean. It should also be understood that the various shapes are intended to conform to the native mitral annulus, but also take into consideration the various deformations and dysfunctions of the ischemic mitral valve.

In a typical mitral annuloplasty remodeling, an annuloplasty ring sized slightly smaller than the distended annulus is implanted. The ring can be downsized one or two sizes, which typically corresponds to a reduction in the major axis dimension of 2 to 4 mm. The annuloplasty rings of the present invention incorporate this reduction by having a 2 to 4 mm reduction of the minor axis dimension as compared to the currently available rings. Desirably, given a predetermined major axis dimension, the ratio of the minor axis dimension to the major axis dimension is less than 3:4 by reducing the absolute value of the minor axis dimension by between about 2-4 mm from an exact 3:4 ratio so as to restore the coaptation between the two leaflets without reducing excessively the overall orifice area of the annuloplasty ring.

Furthermore, the anterior-posterior or minor axis size reduction may be more pronounced in the P3 region so as to further overcorrect the predominant tethering of the posterior leaflet and the dilatation of the annulus in this region. This results in an asymmetrical shape of the ring. It has been discovered that a size reduction along the minor axis effected by reshaping the posterior section of the ring results in more successful leaflet coaptation and generally better clinical results. This configuration differs from some earlier annuloplasty rings that reduced the minor axis dimension by only reshaping the anterior section of the ring.

In some embodiments, the posterior section bows downward in the direction of blood flow to help remodel the mitral annulus in the region of the posterior leaflet scallops P2 and P3 (see FIG. 3b) closer toward the left ventricle LV. With such a configuration the annulus is displaced downward in these segments in order to reduce the distance between the annulus and the papillary muscle and therefore to reduce the stress on the annular sutures.

In FIG. 4 a prosthesis for annular mitral valve according to the prior art is shown. It has a kidney-like or D-shape, and it is made up of an anterior half-ring 1 rectilinear in first approximation, that is sutured in correspondence of the joining of the anterior valve leaflet 2 and a curved posterior half-ring that is sutured in correspondence of the joining of the posterior valve leaflet. The posterior half-ring 2 and anterior half-ring 1 are coupled at two points 5 and 6 located on a transverse plane 3 that define a maximum width section of the prosthesis. In addition a longitudinal plane 4 is also defined, that intersects the prosthesis at the points 7 and 8, that is arranged perpendicular to the transverse plane 3 and equidistant from the coupling points 5 and 6. The posterior half-ring 2 is thus subdivided in a first lateral zone (left) 9 located between the points 5 and 7, and a second lateral zone (right) 10 located between the points 6 and 7. The intersection points 5, 6 and 7, 8 of the prosthesis respectively with the planes 3 and 4 define the terms for the calculation of the dimensions of the prosthesis. According to the known art, the ratio between the distance between the points 7 and 8, herein also defined as the height of the prosthesis, and the distance between the points 5 and 6, herein also defined as the width of the prosthesis, is typically equal to 3:4.

Figure 5:
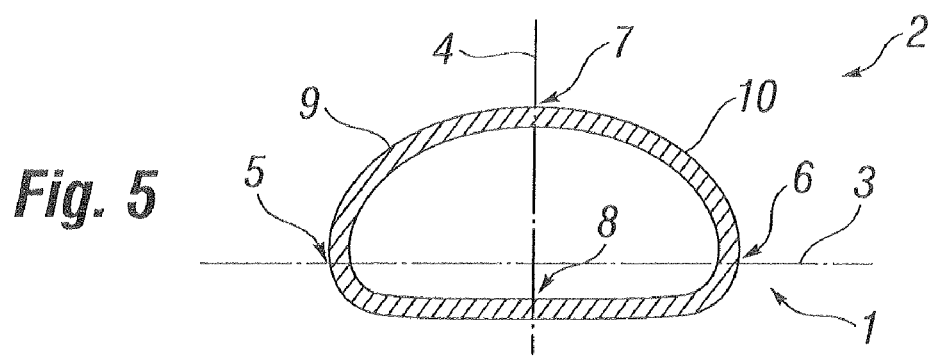
FIG. 5 shows a first embodiment of an annular prosthesis for the mitral valve according to the present invention.

In FIG. 5 a first embodiment of an annular prosthesis for mitral valve according to the present invention is shown. It substantially has the same shape as the one rendered in FIG. 4 but the ratio between the height and the width of the prosthesis is lower than 3:4, for instance equal to 2.5:4 or equal to 2:4.

For every size of prosthesis two or more reduced ratios can therefore be provided. By "size" the dimension of the transverse width of the prosthesis is meant; the "size" represents the clinical parameter on the basis of which the prosthesis is selected in each single clinical case in examination, and it is also the identifying parameter for the prosthesis.

The lower ratio as compared with the prostheses currently used for annuloplastic surgery allows its use in selected cases of pathologies that are not treatable in adequate way with conventional prostheses.

The lower ratios in this case have the function to treat pathologies characterised by reduced movement of the leaflets with tethering (stretching towards the cardiac apex) symmetrical (as regards each leaflet) with medium or serious proportions. The reduction of the ratio confers the prosthesis a more "squeezed" shape, that allows a better apposition of the leaflets in selected cases. For instance, in the dilated cardiomyopathy, when the expansion of the left ventricle determines a lateral movement and toward the apex of the papillary muscles, the leaflets stretch toward the cardiac apex and the apposition is thus lacking at central level. A possible sizing, in addition, must respect an anatomical requirement: the anterior half-ring 1 (the base for the implant of the front leaflet) is anatomically fixed and not modifiable, and therefore, the sizing should not be applied to this structure, that is to the width of the prosthesis. The maintaining of a normal fore width of the prosthesis, associated with the reduction of the height allows an undersizing that is less inclined to deformation of the fore leaflet, therefore reducing the risk of residual insufficiency.

Figure 6:
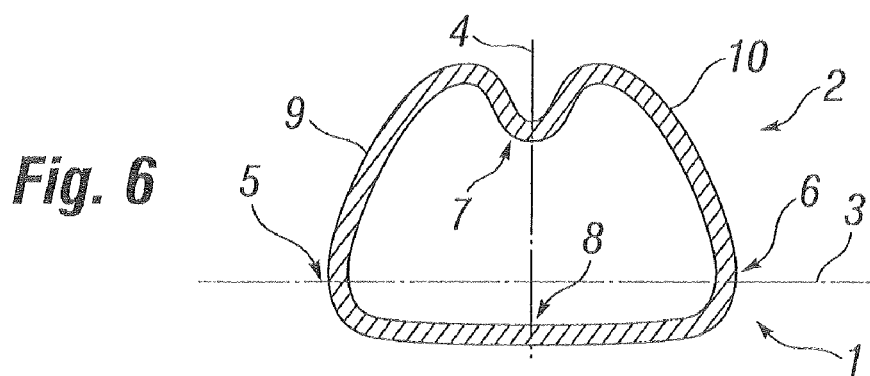
FIG. 6 shows a second embodiment of an annular prosthesis for the mitral valve according to the present invention.

In FIG. 6 a second embodiment of an annular prosthesis for mitral valve according to the present invention is shown. In this case the natural ratio height/width of 3:4 is maintained in order to define the curving radii of the two lateral parts of the anterior half-ring. In the central zone, in proximity of the point 7, the distance between the posterior half-ring 1 and the front half-ring 2 is reduced, with the aim of obtaining a height/width ratio lower than 3:4. The central zone of the posterior half-ring 2 therefore takes a configuration that recalls the dog bone or gull wing shape and increases the coaptation at central level by limiting the annular reduction at level of the commissure.

In some extreme cases, it could be useful to make the distance between the two half-rings in the central zone equal to zero, in order to obtain an eight-shape configuration, in order to improve the coaptation at central level. This remodeling simulates the double orifice operation, in which the leaflets are joined at the center of the valve in order to force the central coaptation. This prosthesis could also be used with this type of technique in order to reduce the stress on the suture and in order to minimize the reduction of the valve area.

Figure 7:
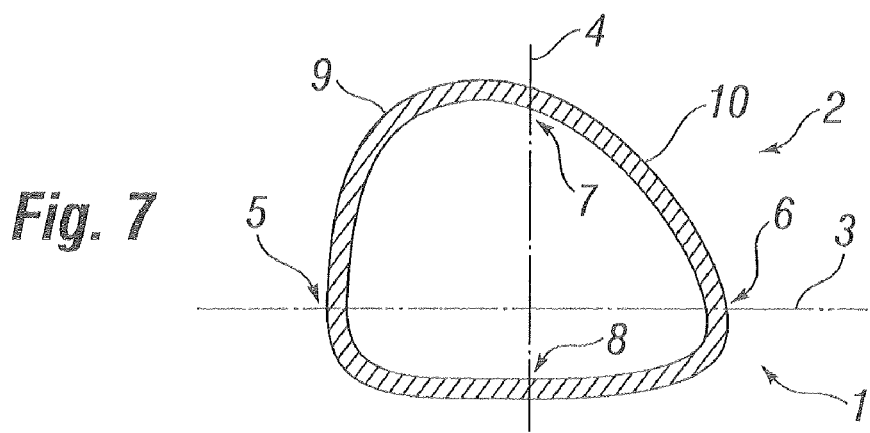
FIG. 7 shows a third embodiment of an annular prosthesis for the mitral valve according to the present invention.

In FIG. 7 a third embodiment of an annular prosthesis for mitral valve according to the present invention is shown. In this embodiment the curving radius of one of the lateral zones, for instance the second lateral zone (right) 10, is increased so as to induce a selective increase of the competence in correspondence of the valve sector with reduced mobility of the leaflets (bad asymmetric apposition of the leaflets as in ischaemic pathology). It is thus obtained that one part of the prosthesis, for instance the first lateral zone (left) 9, maintains a configuration substantially similar to the traditional prosthesis and one part, for instance the second lateral zone (right) 10, gets a sized configuration. In other words the distance between the middle point of the first lateral zone (left) 9 and the longitudinal plane 4 is greater than the distance between the middle point of the second lateral zone (right) 10 and the longitudinal plane.

The prosthesis, according to the present invention, can be made of an inert material that is highly tolerated by the human organism and can have a resistance that is appropriate to the use and that can substantially maintain the shape given to it.

Figure 8:
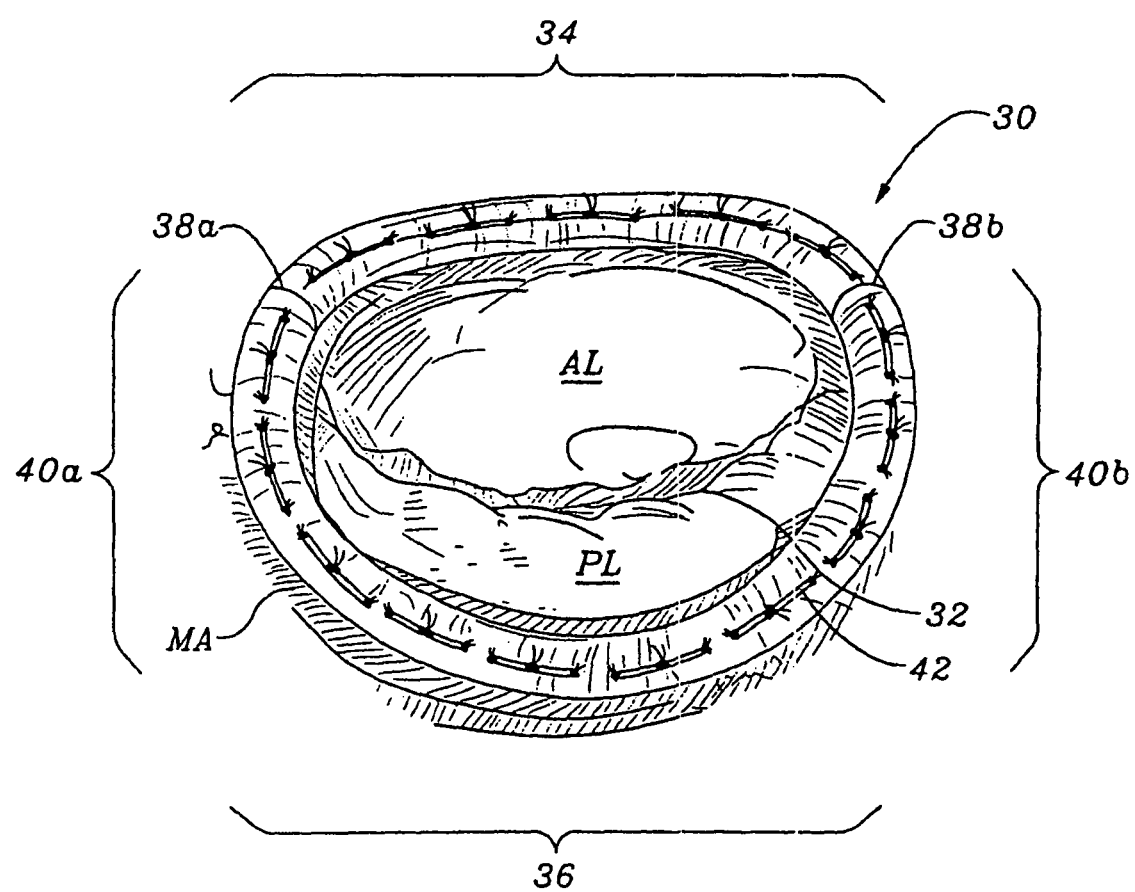
FIG. 8 is a plan view of annuloplasty ring of the present invention implanted so as to restore competency to the mitral valve.

An exemplary annuloplasty ring 30 of the present invention is shown in FIG. 8 implanted around a mitral annulus MA. As described above, the mitral annulus has an anterior leaflet AL and a posterior leaflet PL. When the ring 30 is implanted, the leaflets are brought closer together and supported so that they meet at a coaptation surface 32. The ring 30 thus corrects the problem of functional mitral regurgitation.

The ring 30 has an oval or somewhat D-shaped configuration with a relatively straight anterior section 34 opposite a curved posterior section 36. A pair of trigone or commissure markers 38*a*, 38*b* generally delimit the anterior side 34, while a pair of opposed side sections 40*a*, 40*b* extend between each of these markers and the posterior section 36. A plurality of knotted suture loops 42 are typically used to secure the ring 30 to the mitral annulus MA, although other fasteners such as staples, fibrin glue, or the like may be used.

In the pathological conditions for which the annuloplasty ring 30 is best suited, the posterior aspect of the mitral annulus is depressed relative to the anterior aspect, as is illustrated in FIG. 2. In the view of FIG. 8, the posterior aspect will be depressed into the page relative to the anterior aspect. The annuloplasty ring 30 of the present invention has a shaped posterior section 36 that generally follows the modified shape of the mitral annulus MA. In other words, the posterior section 36 is bowed into the page relative to the anterior section 34. When secured in place with sutures 42, for example, the ring 30 supports the mitral annulus MA in its modified shape, rather than trying to revert the annulus back to the original substantially planar configuration. At the same time, the ring 30 desirably constricts the orifice circumference defined by the annulus so as to bring the anterior leaflet AL and posterior leaflet PL closer together. Because the ring 30 does not pull the posterior aspect of the mitral annulus MA upward from its modified position, high stresses are not set up in the attachment sutures 42 and thus there is less potential for the dehiscence.

FIGS. 9 and 10 illustrate the exemplary annuloplasty ring 30 in perspective above a mitral annulus that is depressed on its posterior side. The bow of the ring 30 in its posterior section 36 is seen best in FIG. 10 mimicking the depression of the posterior aspect of the mitral annulus MA in the pathology encountered with functional mitral regurgitation.

The exemplary annuloplasty ring 30 of FIGS. 8-10 is shown in more detail in FIGS. 11A-11C. The ring 30 is shown complete with a fabric covering. For purpose of orientation, FIG. 11A illustrates orthogonal axes wherein the X- and Y-axes generally define the datum plane 20 as mentioned above with respect to FIGS. 1 and 2. The X-axis extends across the ring 30 from one side 40a to the opposite side 40b at the point of maximum dimension. The X-axis thus defines a major axis of the ring 30. The Y-axis defines a plane of symmetry for the ring 30 extending between a midpoint of the anterior side 34 to a midpoint of the posterior section 36. The Y-axis also defines a minor axis for the ring 30.

As with many conventional rings, the ratio of the minor axis dimension to the major axis dimension is desirably about 3:4. This size ratio is the "classic" shape of the mitral annulus, and may be the best configuration of the annuloplasty ring 30. However, it is contemplated that other shapes that have smaller minor axis-to-major axis ratios may actually increase leaflet coaptation. Although not geometrically precise, the non-circular ring configuration may be considered oval, elliptical or D-shaped. It should be noted that the present invention could also take the form of a discontinuous ring that has a C-shape, for example. The break in such a ring may be in the anterior section, and the posterior section is continuous and exhibits the downward bow as explained.

The Z-axis in FIG. 11B lies along of the axis of blood flow through the ring 30 when implanted, and it will be understood that the positive Z direction is the "upward" direction, the negative Z direction is the "downward" direction, and the ring 30 is designed to be implanted in a mitral annulus such that blood will flow in the downward direction.

Several points are noted around the ring 30 to help describe the posterior bow. These points, and the ones shown in FIGS. 12A-12B, are imaginary center points through the cross-section of the ring 30. Two points A are symmetrically located on either side of the Y-axis at an angular distance θ from the X-axis. The midpoint of the posterior section 36 is denoted B. The ring 30 has a posterior bow such that the point B is at the lowest elevation along the Z-axis. The magnitude of this posterior bow is indicated by the dimension $Z_1$ in FIG. 11C. The points A on either side of the posterior section 36 represent the location where the posterior bow begins. That is, except for the posterior section, the ring 30 is preferably substantially planar. However, the anterior section 34 can optionally be bowed upward by a distance of between about 2-4 mm (0.08-0.16 inches), as in certain rings of the prior art. In the latter example, the posterior section 36 bows downward in the Z-direction relative to the elevation of the trigone markers 38a, 38b.

Various possible configurations for the ring 30 as seen in FIGS. 11A-11C are contemplated, with the dimension $Z_1$ and the angle θ varying between ranges determined by the overall size of the mitral annulus, the extent of anatomical droop of the posterior aspect, and various other factors including surgeon preference. Nevertheless, certain ranges are believed suitable to support and correct a majority of the patients exhibiting the particular anatomical irregularity as described herein. The downward bow or posterior bow preferably extends along a majority of the posterior section 36 between the points A, which points are between 0 and 45° from the X-axis (θ). More preferably, the points A are between 20-40°, and more particularly about 30° from the X-axis. The magnitude of bow $Z_1$ may be between about 2-15 mm (0.08-0.59 inches), and more typically is between about 4-8 mm (0.16-0.31 inches), depending on the size of the ring.

Although the ring 30 is shown in FIGS. 11A-11C as symmetric about the Y-axis, it does not necessarily have to be so. For example, the point B may be displaced from the Y-axis such that the downward bow is not centered in the posterior section 36. An asymmetric ring is shown and described below with reference to FIGS. 13A and 13B.

FIGS. 12A-12C illustrate an alternative annuloplasty ring 50 of the present invention that has both upward and downward bows. Again, the ring 50 is shown complete with a fabric covering. The ring 50 includes an anterior section 52, a posterior section 54, and a pair of side sections (not numbered) therebetween. The ring 50 is generally planar on the anterior section 52 and shaped on the posterior section 54. The points A symmetrically disposed across the Y-axis again denote the locations on each side where the ring 50 begins to curve out of a plane. In this embodiment, the ring curves upward in the Z-direction from the points A, as best seen in FIG. 12B, to high points C, and then dips downward to the midpoint B of the posterior section 54. The downward bow of the ring between points A and B is shown in FIG. 12C as the dimension $Z_2$, which has a magnitude similar to that given for $Z_1$ in FIG. 11C. The upward curve may be selected so as to better match the patient's annulus shape. Furthermore, the anterior section 52 may be upwardly bowed by a distance of between about 2-4 mm (0.08-0.16 inches).

Various permutations of the ring 50 shown in FIGS. 12A-12C are contemplated, with the dimensions being altered based on numerous factors. In an exemplary embodiment, the points A are desirably disposed an angle α from the X-axis of between about 0-15°, and more desirably between about 5-10°. The points C of maximum height of the ring 50 are preferably spaced an angle β from the X-axis of between about 15-45°, and more preferably between about 25-35°. The lowest point B of the ring 50 may be bowed along the Z-axis as in the embodiment of FIGS. 11A-11C, so that, as indicated FIG. 12C, $Z_2$ is desirably between about 2-15 mm (0.08-0.59 inches), and more typically is between about 4-8 mm (0.16-0.31 inches), depending on the size of the ring. Therefore, the total height of the ring 50 is at least 2 mm, and may be greater than 15 mm.

Figure 13B:
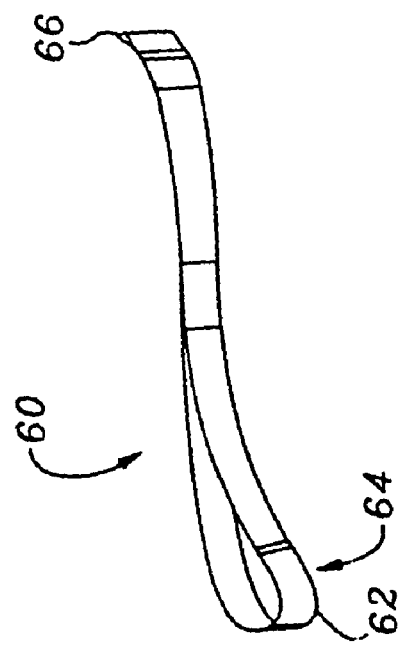
FIGS. 13A and 13B are front and side elevational views, respectively, of an inner ring body of a further annuloplasty ring of the present invention having an off-center posterior bow and an anterior bow.
Figure 13A:
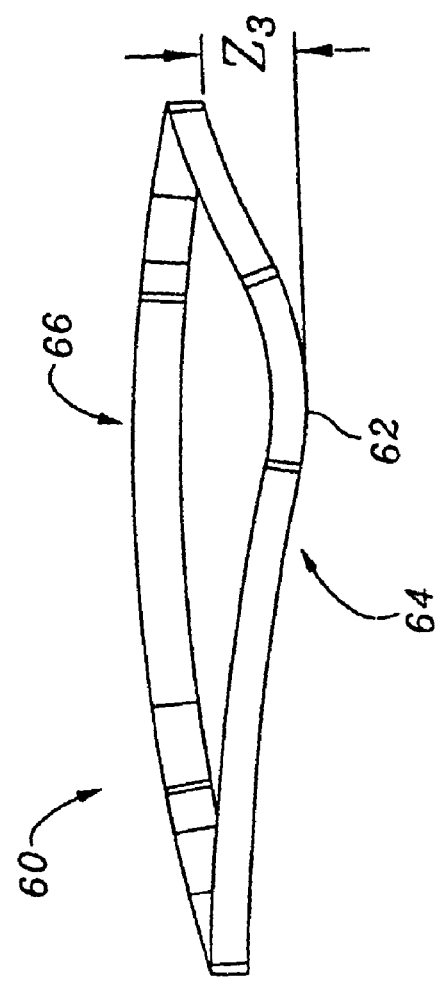

FIGS. 13A and 13B show an inner ring body 60 for use in an annuloplasty ring of the present invention. The ring body 60 has a posterior bow 62 that is offset from the center of a posterior section 64. In the illustrated embodiment, the bow 62 is offset toward the posterio-medial side (to the right) by about 20% of the entire major axis width of the ring body 60. Another way to state the offset is that, in plan view, the bow 62 is centered at a clock position, with 12:00 being centered in the anterior side. In that sense, the bow 62 is centered between 3:00 and 6:00, and more preferably is centered at about 5:00 (using the terminology of FIGS. 15A and 16A, the bow 62 is centered somewhere in the posterior segments P2 and P3, but offset from the center of the P2 segment). The axial magnitude of the downward bow $Z_3$ is shown and may vary from about 2.0 mm (0.08 inches) to about 4.0 mm (0.16 inches), and more preferably from about 3.0 mm (0.12 inches) to about 3.8 mm (0.15 inches), depending on ring size. In addition, the ring body 60 has an anterior section 66 that is upwardly bowed by a distance of between about 2-4 mm (0.08-0.16 inches).

The inner ring body 60 demonstrates an asymmetric ring that conforms to patients that have a posterior annular bow that is displaced from the midline. It is believed that most patients have such a malformed anatomy resulting from the pathologic conditions described herein. However, posterior bows that are centered or even offset to the left have been observed. Therefore, one configuration of ring that is embodied in the present invention is one that is pre-shaped with a posterior bow in the middle or to the right, and that is malleable so that the bow can be exaggerated or diminished by the surgeon after examination of the precise shape of the patient's annulus. Further, in such a convertible ring the bow can even be displaced, from the right to the left, for example. Although the material of the ring permits manual deformation, it would be stiff enough to withstand further deformation once implanted and subjected to normal physiologic stresses.

The ring preferably includes an inner ring body and an outer sewing sheath that permits the ring body to be sutured into the mitral annulus. The sewing sheath should be sufficiently porous and/or flexible to permit sutures to be passed therethrough. One exemplary construction is to enclose the inner ring body in a tubular sheath of suture-permeable material, such as silicone, which is then covered with a fabric tube, such as polyethyl terapthalate.

As opposed to flexible annuloplasty rings that are designed simply to reduce the circumference of the mitral annulus, the annuloplasty ring of the present invention must be at least semi-rigid. It must retain its posterior bow in opposition to the stresses that will be imparted by muscles of the heart throughout each beating cycle. For example, the ring body may be made from materials such as Elgiloy (a cobalt-nickel alloy), titanium, or Nitinol (a nickel-titanium alloy). Exemplary ring constructions are seen in the CARPENTIER-EDWARDS CLASSIC Annuloplasty Ring, and in the CARPENTIER-EDWARDS PHYSIO Annuloplasty Ring, both made and sold by Edwards Lifescience of Irvine, Calif.

Figure 14:
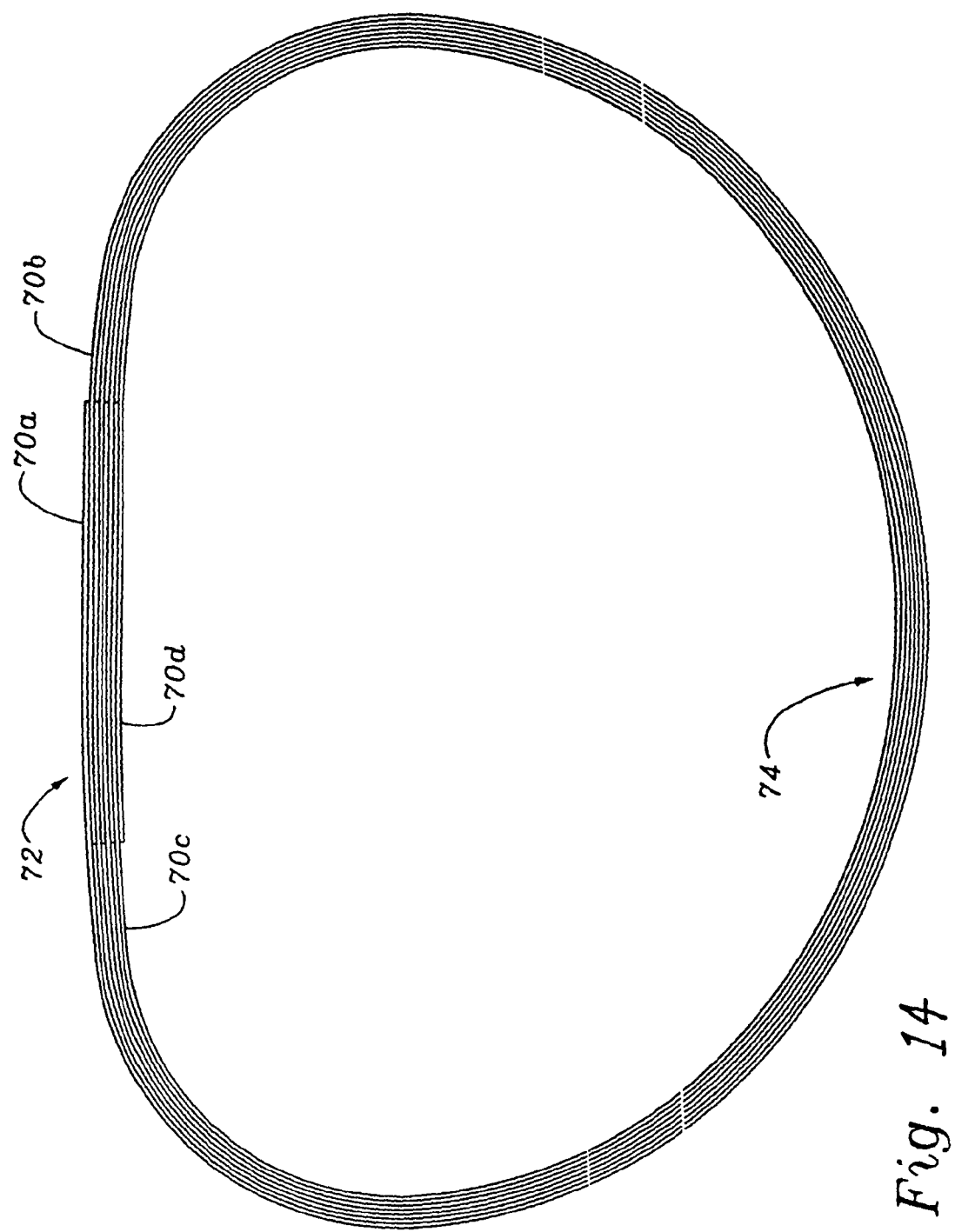
FIG. 14 is a top plan view of an inner ring body of an annuloplasty ring of the present invention showing details of a composite band construction.

FIG. 14 illustrates one exemplary construction of the inner body of the annuloplasty rings of the present invention that utilizes multiple flat bands of Elgiloy in a composite structure. Specifically, there are four bands 70a, 70b, 70c, and 70d from the outside to the inside. The four bands are concentrically disposed in the shape of the ring. Each band is a flat strip of material having a width of between about 1.4-2.0 mm (0.056-0.078 inches). In one embodiment, the bands 70 overlap in the anterior section 72 of the ring body and are fastened together by, for example, spot welding at multiple points. The width of each strip may also be greater in the anterior section 72 than in a posterior section 74, which means that the ring body is more flexible in the posterior section than in any other section. Although not shown, a plurality of strips of protective film is used in between each band 70, and on the outer face of the outer band 70a. The strips may be a polymer such as Mylar. The strips help reduce rubbing between the bands 70 and also deflect suture needles from the outer band 70a and thus prevent scratching thereto.

It will also be readily apparent that supporting the mitral valve annulus with the present annuloplasty ring will maintain the posterior leaflet depressed below the anterior leaflet, and thus the area of coaptation therebetween will be different than in a healthy valve. This is required by the pathology of the ventricle with displacement of the papillary muscles and posterior leaflet. However, those of skill in the art will recognize that this slight realignment of the leaflets is acceptable because of the surplus area of the leaflets available for coaptation, and because the realignment will be offset by other changes to the shape of the annulus that should over time improve coaptation of the two leaflets and therefore decrease regurgitation.

A further exemplary embodiment of an annuloplasty ring 130 of the present invention is seen in FIGS. 15A and 15B.

FIG. 15A is a so-called atrial plan view because it visualizes the ring 130 along a flow axis 132 from the atrial side. That is, blood flow will be into the page through the ring 130 as seen in FIG. 15A, and downward in FIG. 15B.

The annuloplasty ring 130 is shown fully constructed with an external fabric covering (not numbered) over an internal ring body. It will be understood that the flexible fabric covering adds relatively little to the overall shape of the ring 130, and therefore the configuration depends on the shape of the internal ring body. Therefore, when the various shapes of the rings herein are described it is really the shapes of the ring bodies that are referenced.

The annuloplasty ring 130 comprises an anterior section AS defined between an anterolateral trigone T1 and posteriomedial trigone T2, with the remainder of the ring defined between the trigones by a posterior section made up of three sequential segments: P1, P2, and P3. The annuloplasty ring 130 is generally oval-shaped with a longer dimension along a major axis 134, a shorter dimension along a minor axis 136. The minor axis 136 intersects both the anterior section AS and the posterior segment P2. In a preferred embodiment, the minor axis 136 bisects both the anterior section AS and the posterior segment P2.

As seen in FIG. 15B, the annuloplasty ring 130 lies substantially in the plane defined by the major and minor axes 134, 136, which plane is desirably perpendicular to the flow axis 132. In an alternative embodiment, the anterior section AS may be deflected upward (with respect to the flow axis 132) as seen by the dashed line indicated as AS'. This upwardly deflected anterior section AS' provides a desirable three dimensional configuration which conforms to the upwardly bowed anterior aspect of the mitral annulus.

With reference again to FIG. 15A, four radial lines 140a, 140b, 140c, 140d emanate outward from the flow axis 132 to indicate the dividing lines between the anterior section AS and the posterior segments P1, P2, and P3. The anterior section AS can be fairly accurately located between the trigones T1 and T2, which are typically marker threads that correspond to the positions of the native trigones or commissures such as seen in FIG. 3a. On the other hand, the posterior segments P1, P2, and P3 are shown somewhat schematically as circumscribing particular arcs around the periphery of the posterior section. The magnitude of the arcs defined by the posterior segments P1, P2, and P3 may vary depending on a variety of factors, including actual measurement of the mitral valve posterior leaflet scallops, and surgeon preference. As a rule, however, the major axis 134 intersects both the first and second posterior segments P1 and P3, and the minor axis 136 intersects the middle posterior segment P2.

The annuloplasty ring 130 has an asymmetric configuration across the minor axis 136 with the convexity of the P1 segment of the posterior section being greater than the convexity of the P3 segment. In particular, a portion of the P3 side is pulled in toward the center of the ring so as to define an oblique inner dimension line 142a that is shorter than an oblique inner dimension line 142b. The dimension lines 142a, 142b are measured from a point 144 on the minor axis 136 on the middle inner edge of the anterior section AS. The dimension line 142a is drawn to the point in the P3 zone that is closest to the point 144 at the middle of the anterior section AS, and forms an angle θ with the minor axis 136. The dimension line 142b is also oriented at an angle θ from the minor axis 136 but in the opposite rotational direction form the line 142a.

Stated another way, the annuloplasty ring 130 has a generally oval shape except for a reduced curvature portion 150 extending between a point 152 at the intersection of the minor axis 136 and the posterior segment P2, and the second trigone T2. "Reduced curvature" is relative to the curvature of the opposite side of the ring 130 across the minor axis 136; namely, relative to the segment P1 and the left side of segment P2. The conventional "oval" shape of the ring 130 is illustrated by a dashed line extension 154 around the modified portion of the ring, and the divergence of the reduced curvature portion 150 is apparent. The reduced curvature portion 150 is shown extending through approximately half of the central posterior segment P2 and all of the third posterior segment P3. Alternatively, the central posterior segment P2 could continue the oval shape of the remainder of the ring 130 and the reduced curvature portion 150 could extend only from imaginary point 156 to the second trigone T2. The reduced curvature portion 150 is desirably less convex than the imaginary oval shape 154, but may even be linear, or even slightly concave.

The effect of providing the reduced curvature portion 150 of the P3 segment, is to remodel the mitral annulus in the region of the posterior leaflet scallop P3 (see FIG. 3b) closer toward the flow axis than the other scallops. The reduction of the anterior-posterior dimension of the mitral annulus in this manner is believed to more effectively correct for dysfunctions that exist in ischemic mitral valve insufficiency.

FIGS. 16A-16C are plan and elevational views of an alternative annuloplasty ring 160 of the present invention also configured to correct for all dysfunctions that exist in ischemic mitral valve insufficiency. As with the earlier described ring 130, the annuloplasty ring 160 is generally oval shaped around a flow axis 162, and with respect to a major axis 164 and a minor axis 166. The ring 160 has an anterior section AS defined between two trigones T1 and T2, and a posterior section extending around the remainder of the ring between the trigones and composed of three sequential segments: P1, P2, and P3.

The annuloplasty ring 160 lies substantially in a plane (or in a saddle-shaped three-dimensional surface) except for a portion 170 of the posterior section located within the P2 and P3 segments that is deflected downward with respect to the flow axis 162. As seen best in FIG. 16B, the downwardly deflected portion 170 includes an apex A which is the lowest elevation of the ring 160. The downwardly deflected portion 170 is desirably exclusively within the P2 and P3 segments and is shown to extend from point B to point C around posterior section. Point B desirably lies at the intersection between the first and second posterior segments P1 and P2, while point C desirably lies at the intersection of the major axis 164 and the third posterior segment P3. The exact location of points A, B, and C may vary as long as the deflected portion 170 exists in the posterior section of the ring 160 and primarily outside of the first posterior segment P1.

In preferred embodiment, the apex A of the deflected portion 170 is off-center toward the P1 segment such that, as seen in FIG. 16B, a transition 172 between points A and B extends along a shorter distance around the ring 160 than a transition 174 between points A and C. More preferably, the transition 174 between points A and C is almost linear as shown. The effect of providing the downwardly deflected portion 170 and elongated transition 174 is to remodel the mitral annulus in the region of the posterior leaflet scallops P2 and P3 (see FIG. 3b) closer toward the left ventricle LV so as to displace downward the annulus in these segments in order to reduce the increased distance h' between the annulus and the papillary muscle and to reduce the stress on the annular sutures.

The anterior section AS is shown in FIG. 16A as being linear, but an alternative configuration is shown in dashed line at AS'. The alternative anterior section AS' is deflected slightly inward along the minor axis 166 and thus reduces the anterior-posterior dimension of the ring 160. As mentioned above, the reduced curvature portion 150 of the ring 130 in FIG. 15A can also be combined with the downwardly deflected portion 170 to further reduce the anterior-posterior dimension.

A further exemplary embodiment of an annuloplasty ring 180 of the present invention is seen in FIGS. 17A in 17B. The nomenclature used above with respect to the sections and segments around the ring are consistent. The ring 180 is similar in many respects to the ring 160 seen in FIGS. 16A-16C in that incorporates a downwardly deflected portion 182 in the posterior section. Again, the deflected portion 182 has an apex A which is off-center with respect to the minor axis (not shown) of the ring 180 toward the P1 segment of the posterior section. Indeed, the inventors have determined that a combination of a downward deflection in the posterior side and either a reduced anterior-posterior dimension or an obliquely (asymmetrically) pulled-in posterior section is particularly effective for correcting ischemic mitral valve insufficiency (IMVI). It should be noted that any combination of these features whether or not they are described independently herein, is not encompassed by the present invention.

The annuloplasty ring 180 is substantially saddle-shaped as opposed to being substantially planar. That is, the posterior segments P1 and P3 rise upward from a reference plane 184 while the anterior section AS lies generally on the reference plane. If the ring 180 were completely saddle-shaped, the central posterior segment P2 would also lie on the reference point. Instead, the downwardly deflected portion 182 brings the posterior segment P2 below the reference plane 184. It should be understood, therefore, that the portion 182 deflects downward from the saddle-shaped remainder of the ring 180.

In a preferred construction, the annuloplasty ring bodies of the several rings of the present invention are constructed to be more flexible in the posterior section than in the anterior section AS. For example, the ring body may be constructed with a metallic core of different thickness or with a series of annular bands that overlap in the anterior section to render that section less flexible than in the posterior section. In an alternative construction the ring is completely rigid throughout.

FIGS. 18A-18G illustrate a series of annuloplasty rings 200a-200g of the present invention that are sized for different patients. The drawings are dimensionally accurate for a series of prototypes that are shown in atrial plan view. Each ring can be made in one plane or can have a saddle shape, such as the annuloplasty ring 180 of FIGS. 17A-17B. That is, the posterior segments P1 and P3 (noted only in FIG. 18F) may rise upward with respect to the posterior segment P2 and anterior section AS.

Figure 18A:
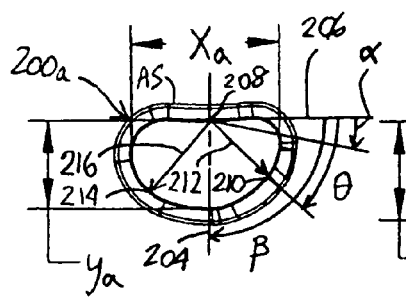
FIGS. 18A-18G are atrial plan views of a series of dimensionally accurate prototypical annuloplasty rings of the present invention sized for different patients.
Figure 18B:
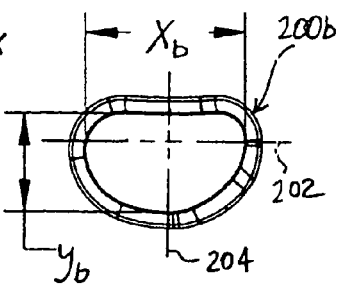
Figure 18C:
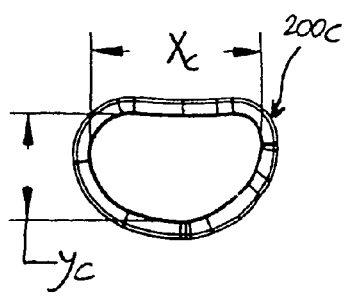
Figure 18D:
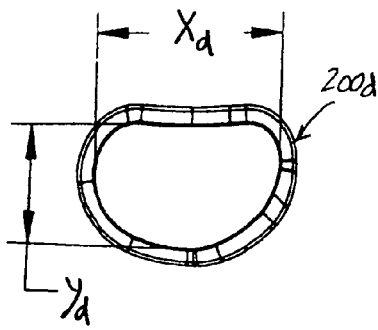
Figure 18E:
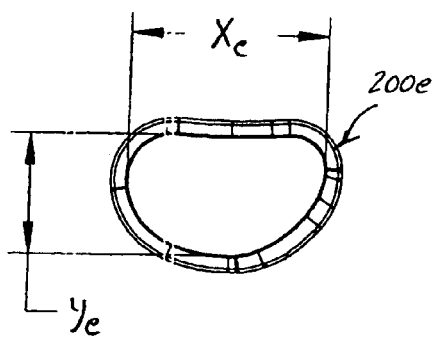
Figure 18F:
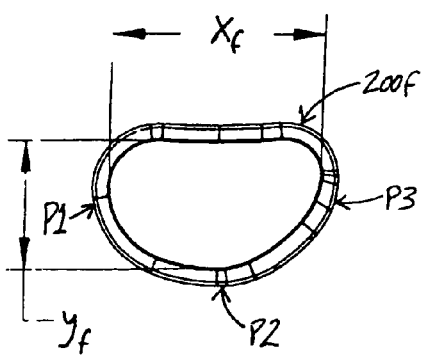

The major axis 202 and minor axis 204 are shown for ring 200b in FIG. 18B, and the same orientation applies to each ring 200a-200g. The dimension $x_i$ along the major axis 202 and dimensions $y_i$ along the minor axis 204 are denoted for each ring 200a through 200g. The following table provides these dimensions, as well as the labeled ring size that would be used for selecting a specific ring. That is, a Size 34 ring is the label for a ring destined to be implanted in a patient having a measured native annulus, or surgeon-determined annulus, of about 34 mm along the major axis. These dimensions are measured per convention between the inner surfaces of each ring along the respective axes.

TABLE I

Dimensions of Annuloplasty Rings of FIGS. 18A-18G

| Ring | Ring Size | Major Axis, $x_i$ (in./mm) | Minor Axis, $y_i$ (in./mm) | Ratio of $y_i/x_i$ (%) |
|---|---|---|---|---|
| 200a | 24 | 0.885/22.5 | 0.534/13.6 | 60.3 |
| 200b | 26 | 0.961/24.4 | 0.580/14.7 | 60.3 |
| 200c | 28 | 1.036/26.3 | 0.626/15.9 | 60.4 |
| 200d | 30 | 1.112/28.2 | 0.672/17.1 | 60.4 |
| 200e | 32 | 1.187/30.1 | 0.719/18.3 | 60.6 |
| 200f | 34 | 1.263/32.1 | 0.765/19.4 | 60.6 |
| 200g | 36 | 1.338/34.0 | 0.811/20.6 | 60.6 |

As mentioned above, the minor axis dimensions $y_i$ are reduced for each ring such that the ratio of the minor axis dimension to the major axis dimension is less than 3:4 (or less than 75%). In absolute terms, this is a reduction of between about 2-4 mm from an exact 3:4 ratio so as to restore the coaptation between the two leaflets without reducing excessively the overall orifice area of the annuloplasty ring. For example, Size 24 ring 200a of FIG. 18A has a major axis dimension $x_a$ of 0.885 in. (22.5 mm). A precise 3:4 minor/major axis ratio would result in a minor axis dimension of 0.664 in. (16.9 mm). However, the minor axis dimension $y_a$ is 0.534 in. (13.6 mm), a reduction from the exact 3:4 ratio of about 3.3 mm.

Viewed another way, each ring 200a-200g has a minor axis dimension reduction of about 14% from the conventional or normal ring size. This is approximately equivalent to a reduction of about one ring size (e.g., a Size 26 ring to a Size 24 ring is one ring size reduction). However, the use of the rings of the present invention is not the same as the current "downsizing" practice because the ring that is ultimately used is not labeled as a smaller sized ring. For instance, current practice may be to "downsize" and use a Size 24 ring for a measured Size 26 patient. Ring 200b of FIG. 18B would be the selected ring in accordance with the present invention for a Size 26 patient. Ring 200b is labeled as a Size 26 ring, although it is downsized in dimension from the conventional ring size. Therefore, there is no uncertainty about which ring to select—a size 26 ring is for a Size 26 patient. Also, conventional practice leaves no "downsizing" choice for small patients with annulus sizes of 24 mm. That is, there is typically no Size 22 ring available. The Size 24 ring 200a of the present invention, on the other hand, is already downsized, and provides the improved coaptation results previously mentioned for indicated patients.

Most significantly, however, downsizing reduces the entire ring periphery when often only a segment of the mitral annulus need be corrected. For instance, an asymmetric dilation such as seen in FIG. 3b requires correction of only a portion of the posterior aspect, in the region of the P2-P3 leaflet scallops. Simply implanting a smaller ring would correct the affected region but would also constrict the healthy regions, and in particular can overly stress the more fibrous anterior aspect which typically does not change size or shape. Rings of the present invention account or the selective peripheral downsizing required due to certain pathologies such as ischemic mitral regurgitation.

It should also be noted that the dimensions along the major axes of each ring are less than the measured or otherwised determined annulus size, in keeping with one of the aspects of the invention, which is downsizing the entire ring, not just the anterior-posterior dimension. The desired absolute major axis dimension reduction is between about 1.0-1.5 mm. For example, the convention or normal major axis dimension for Size 24 ring 200a of FIG. 18A is about 24 mm. However, ring 200a of FIG. 18A has an actual major axis dimension $x_a$ of 0.885 in. (22.5 mm), which is a reduction of about 1.5 mm, or about 6%. One of skill in the art will appreciate the difference between selecting a "downsized" ring of the same proportional 3:4 size ratio and using the rings of the present invention. Namely, conventional practice of "downsizing" for a Size 26 patient would dictate using a conventional Size 24 ring, with a 24 mm major axis and an 18 mm minor axis (a 3:4 ratio). The Size 26 ring of the present invention, on the other hand, has a 24.4 mm major axis and a 14.7 mm minor axis (a 3:5 ratio).

All of the annuloplasty rings 200a-200g shown in FIGS. 18A-18G have the asymmetry previously noted wherein the P3 segment (see FIG. 18F) corresponding to the P3 leaflet has a reduced curvature relative to the P1 segment (or, the convexity of the P1 segment is greater than that of the P3 segment). This asymmetry was shown and described above with respect to the ring 130 of FIGS. 15A and 15B.

Figure 18G:
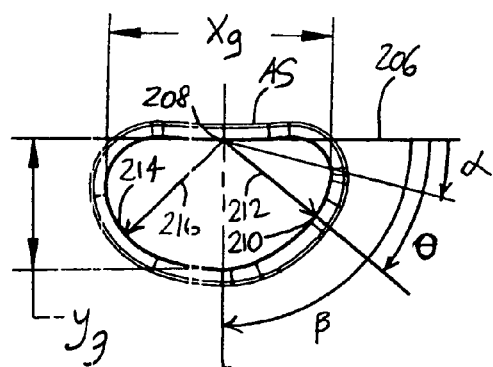

Looking at two particular examples, FIGS. 18A and 18G illustrates a Size 24 ring 200a and a Size 36 ring 200g, respectively, that have a reduced curvature, or "pulled-in", length generally along the P3 segment. The length along each ring 200a-200g that is pulled in is desirably within a particular arc around the ring periphery that is located within the P2 and P3 segments. A horizontal line 206 is drawn along the inner surface of the anterior segment AS of the rings, and three angles α and β are shown extending clockwise therefrom about a central reference point 208 along the minor axis 204. The "pulled-in" length, or length of reduced convexity in comparison to the opposite side of the ring, is located between the angles α and β. For the ring 200a of FIG. 18A, α is 23.2° and β is 90°. For the ring 200g of FIG. 18G, α is 15.8° and β is 90°. The angle β lies along the minor axis 204 and intersects the posterior side of the ring. These are the outer bounds of the rings 200a-200g so that a ranges between 15.8-23.2°, and the "pulled-in" length is between about 57-74° extending counter-clockwise from the intersection of the minor axis 204 and the posterior side of the ring.

A third angle θ is also drawn in FIGS. 18A and 18G which indicates the angle at which the distance along the "pulled-in" length of the ring periphery and the central reference point 208 is least. That is, the point 210 is the closest of any point along the "pulled-in" length to point 208, and the distance is indicated by dimension line 212. A further point 214 is indicated on the ring periphery but on the side opposite point 210 across the minor axis 204 (in the P1 segment). The point 214 is located at the same angle θ from the horizontal line 206 about the central reference point 208 but in the counter-clockwise direction. These lines 212, 216 are drawn along lines emanating between the respective segments and the intersection of the anterior section and the minor axis. Line 216 indicates the "normal" dimension between points 208 and 214. In a preferred embodiment, the ratio of the "pulled-in" dimension 212 to the "normal" dimension 216 is about 0.89 (89%), and the angle θ is about 51°. For ring 200a, dimension 212 is about 0.503 in. (12.8 mm) and the dimension 216 is about 0.564 in. (14.3 mm), a ratio of about 89%. For ring 200g, dimension 212 is about 0.754 in. (19.2 mm) and the dimension 216 is about 0.846 in. (21.5 mm), again for a ratio of about 89%.

The annuloplasty rings 130, 160, 180, or 200a-200g are secured to the patient's annulus using sutures placed in the annulus and then in a sewing cuff which is part of the ring itself. A sewing cuff in this sense means any suture-permeable material or combination thereof that is an integral part of the ring and which is large enough to receive at least a single row of sutures. In conventional models, the sewing cuff is about 2-5 mm wide on the outer periphery of the annuloplasty ring and accommodates a single row of sutures.

For instance, FIGS. 19A-19B illustrate an annuloplasty ring 250 having a shape similar to that of the ring 130 of FIGS. 15A and 15B, and show a single row suture line 252 around the periphery. The cross-section of FIG. 19B illustrates a sewing cuff 254 and an internal structural component 256 of the ring 250 that is typically a wire or band of stainless steel, titanium, or other suitable material.

FIGS. 20A-20B illustrate a preferred construction of an annuloplasty ring 260 that is particularly suited for repair of an annulus afflicted by ischemic disease. Again, the ring 260 has a shape approximately like that of the ring 130 of FIGS. 15A and 15B. FIG. 20B shows a sewing cuff 262 on an outer periphery of the ring 260 that is radially wider than the cuff 254 of FIGS. 19A-19B. In an exemplary embodiment, the sewing cuff 262 has a radial dimension r of between about 5-10 mm. As seen in FIG. 19A, the larger sewing cuff 262 accommodates a double row of suture lines, as indicated by a row of markers 264 as a guide to the surgeon. This provides a more secure fixation of the ring 260 to the diseased annulus and helps prevent dehiscence.

FIGS. 21A-21C show an alternative annuloplasty ring 270 of the present invention that includes a suture cuff area 272 in the P3 region that is radially enlarged in comparison to the remaining suture cuff 274. The P3 region is often the most distended and fragile portion of the native annulus and thus the enlarged suture cuff area 272 provides a more secure fixation of the ring 270 to the diseased annulus and helps prevent dehiscence at that location. The majority of the suture cuff 274 may be between about 2-5 mm in radial dimension while the suture cuff area 272 is between about 5-10 mm. Of course, such a configuration with less than the whole and only a segment of the periphery of the sewing cuff being enlarged is applicable to other disease states or even surgeon preference, and therefore the suture cuff area 272 can be located other than in the P3 region.

It will also be appreciated by those of skill in the relevant art that various modifications or changes may be made to the examples and embodiments of the invention described in this provisional application, without departing from the intended spirit and scope of the invention. In this regard, the particular embodiments of the invention described herein are to be understood as examples of the broader inventive concept disclosed in this application.

What is claimed is:

1. An annuloplasty ring for implantation in a mitral valve annulus designed to correct ischemic mitral valve insufficiency, the native mitral valve being located at the orifice between the left atrium and left ventricle and having two leaflets which coapt to form a one-way valve within an overall orifice area, the annuloplasty ring comprising:

a generally oval shaped ring body having a metallic core and oriented about a central flow axis, the flow axis defining an upward direction and a downward direction, the downward direction corresponding to the direction of blood flow through the mitral valve annulus from the left atrium to the left ventricle, and wherein in plan view as seen along the flow axis the ring body has a major axis perpendicular to a minor axis, the major and minor axes being perpendicular to the flow axis, the ring body having, in atrial plan view, an anterior section generally defined between an anterolateral trigone and a posteromedial trigone, and a posterior section around the remaining periphery of the ring body and between trigones, the posterior section being divided into three sequential segments, (P1), (P2), and (P3), starting from the anterolateral trigone and continuing in a counter-clockwise direction, wherein the minor axis intersects both the anterior section and the (P2) segment of the posterior section, and wherein a portion of the posterior section deflects downward with respect to the remaining sections of the ring body to a single apex; and, wherein, given a predetermined major axis dimension, the ratio of the minor axis dimension to the major axis dimension is less than 3:4.

2. The annuloplasty ring of claim 1, wherein the ring body in plan view has an asymmetric configuration across the minor axis with the convexity of the (P1) segment of the posterior section being greater than the convexity of the (P3) segment.

3. The annuloplasty ring of claim 2, wherein the (P3) segment has a convexity that is pulled-in by about 89% in comparison to the convexity of the (P1) segment as measured along lines emanating between the closest points along the respective segments and a central reference point at the intersection of the anterior section and the minor axis.

4. The annuloplasty ring of claim 1, wherein the portion of the posterior section that is deflected downward is located exclusively within the (P2) and (P3) segments.

5. The annuloplasty ring of claim 1, wherein the portion of the posterior section that is deflected downward is located within the (P2) and (P3) segments, and wherein the apex in the downwardly deflected portion is the lowest elevation of the ring body, and wherein the apex is off-center in the downwardly deflected portion toward the (P1) segment of the ring body such that, in a posterior elevational view, a transition of the ring body between the (P1) segment and the apex extends along a shorter distance around the ring body than a transition of the ring body between the apex and the remaining portion of the (P3) segment.

6. The annuloplasty ring of claim 5, wherein in posterior elevational view the transition of the ring body between the apex and the remaining, generally planar portion of the (P3) segment is substantially linear.

7. The annuloplasty ring of claim 1, wherein in atrial plan view the (P3) segment is substantially linear.

8. The annuloplasty ring of claim 1, wherein the ring body is constructed to be more flexible in the posterior section than in the anterior section.

9. The annuloplasty ring of claim 1, wherein the dimension of the ring body is reduced along the minor axis by an inwardly deflected portion in the anterior section.

10. The annuloplasty ring of claim 1, further including a sewing cuff around the ring body having an enlarged portion around the periphery of the ring body that can accommodate two radially adjacent rows of suture lines.

11. The annuloplasty ring of claim 10, further including markings provided on the sewing cuff to indicate placement of the two radially adjacent rows of suture lines.

12. The annuloplasty ring of claim 10, wherein the enlarged portion of the sewing cuff extends around less than the entire periphery of the ring.

13. The annuloplasty ring of claim 12, wherein the enlarged portion is at least partly in the (P3) segment.

14. The annuloplasty ring of claim 1, wherein the ratio of the minor axis dimension to the major axis dimension is made less than 3:4 by reducing the absolute value of the minor axis dimension by between about 2-4 mm from an exact 3:4 ratio so as to restore the coaptation between the two leaflets without reducing excessively the overall orifice area of the annuloplasty ring.

15. The annuloplasty ring of claim 1, wherein the ratio of the minor axis dimension to the major axis dimension is about 3:5.

16. The annuloplasty ring of claim 1, wherein the metallic core is titanium.

17. The annuloplasty ring of claim 1, wherein the metallic core comprises concentric bands.

18. An annuloplasty ring for implantation in a mitral valve annulus designed to correct ischemic mitral valve insufficiency, the native mitral valve being located at the orifice between the left atrium and left ventricle and having two leaflets which coapt to form a one-way valve within an overall orifice area, the annuloplasty ring comprising:

a generally oval shaped ring body having a metallic core and oriented about a central flow axis, the flow axis defining an upward direction and a downward direction, the downward direction corresponding to the direction of blood flow through the mitral valve annulus from the left atrium to the left ventricle, and wherein in plan view as seen along the flow axis the ring body has a major axis perpendicular to a minor axis, the major and minor axes being perpendicular to the flow axis, the ring body having in atrial plan view an anterior section generally defined between an anterolateral trigone and a posteromedial trigone, and a posterior section around the remaining periphery of the ring body and between trigones, the posterior section being divided into three sequential segments, (P1), (P2), and (P3), starting from the anterolateral trigone and continuing in a counter-clockwise direction, wherein the minor axis intersects both the anterior section and the (P2) segment of the posterior section; and, wherein a portion of the posterior section deflects downward with respect to the remaining sections of the ring body, and wherein the ring body in plan view has an asymmetric configuration across the minor axis with the convexity of the (P1) segment of the posterior section being the greater than the convexity of the (P3) segment.

19. The annuloplasty ring of claim 18, wherein the (P3) segment has a convexity that is pulled-in by about 89% in comparison to the convexity of the (P1) segment as measured along lines emanating between the closest points along the respective segments and a central reference point at the intersection of the anterior section and the minor axis.

20. The annuloplasty ring of claim 18, wherein the downwardly deflected portion of the ring body is located within the (P2) and (P3) segments.

21. The annuloplasty ring of claim 20, wherein the downwardly deflected portion including an apex which is the lowest elevation of the ring body, and wherein the apex is off-center in the downwardly deflected (P2) portion toward the (P1) segment of the ring body such that, in a posterior elevational view, a transition of the ring body between the non-downwardly-deflected (P1) segment and the apex extends along a shorter distance around the ring body than a transition of the ring body between the apex and a non-downwardly-deflected portion of the (P3) segment.

22. The annuloplasty ring of claim 21, wherein in posterior elevational view the transition of the ring body between the apex and the non-downwardly-deflected portion of the (P3) segment is substantially linear.

23. The annuloplasty ring of claim 21, wherein in atrial plan view the (P3) segment is substantially linear.

24. The annuloplasty ring of claim 18, wherein the ring body is rigid.

25. The annuloplasty ring of claim 18, wherein the ring body is constructed to be more flexible in the posterior section than around the remainder of the ring body.

26. The annuloplasty ring of claim 18, wherein the dimension of the ring body is reduced along the minor axis by an inwardly deflected portion in the anterior section.

27. The annuloplasty ring of claim 18, further including a sewing cuff around the ring body having an enlarged portion around the periphery of the ring body that can accommodate two radially adjacent rows of suture lines.

28. The annuloplasty ring of claim 27, further including markings provided on the sewing cuff to indicate placement of the two radially adjacent rows of suture lines.

29. The annuloplasty ring of claim 27, wherein the enlarged portion of the sewing cuff extends around less than the entire periphery of the ring.

30. The annuloplasty ring of claim 29, wherein the enlarged portion is at least partly in the (P3) segment.

31. The annuloplasty ring of claim 18, wherein the ratio of the minor axis dimension to the major axis dimension is less than 3:4.

32. The annuloplasty ring of claim 31, wherein the ratio of the minor axis dimension to the major axis dimension is about 3:5.

33. The annuloplasty ring of claim 18, wherein the metallic core is titanium.

34. The annuloplasty ring of claim 18, wherein the metallic core comprises concentric bands.

35. An annuloplasty ring for implantation in a mitral valve annulus designed to correct ischemic mitral valve insufficiency, the native mitral valve being located at the orifice between the left atrium and left ventricle and having two leaflets which coapt to form a one-way valve within an overall orifice area, the annuloplasty ring comprising:

a generally oval shaped ring body having a metallic core and oriented about a central flow axis, the flow axis defining an upward direction and a downward direction, the downward direction corresponding to the direction of blood flow through the mitral valve annulus from the left atrium to the left ventricle, and wherein in plan view as seen along the flow axis the ring body has a major axis perpendicular to a minor axis, the major and minor axes being perpendicular to the flow axis, the ring body having in atrial plan view an anterior section generally defined between an anterolateral trigone and a posteromedial trigone, and a posterior section around the remaining periphery of the ring body and between trigones, the posterior section being divided into three sequential segments, (P1), (P2), and (P3), starting from the anterolateral trigone and continuing in a counter-clockwise direction, wherein the minor axis intersects both the anterior section and the (P2) segment of the posterior section; and, wherein a portion of the posterior section located exclusively within the (P2) and (P3) segments deflects downward with respect to the remaining sections of the ring body.

36. The annuloplasty ring of claim 35, wherein the downwardly deflected portion including an apex which is the lowest elevation of the ring body, and wherein the apex is off-center in the downwardly deflected portion toward the (P1) segment of the ring body such that, in a posterior elevational view, a transition of the ring body between the non-downwardly-deflected (P1) segment and the apex extends along a shorter distance around the ring body than a transition of the ring body between the apex and a non-downwardly-deflected portion of the (P3) segment.

37. The annuloplasty ring of claim 36, wherein in posterior elevational view the transition of the ring body between the apex and the non-downwardly-deflected portion of the (P3) segment is substantially linear.

38. The annuloplasty ring of claim 36, wherein in atrial plan view the (P3) segment is substantially linear.

39. The annuloplasty ring of claim 35, wherein the metallic core is titanium.

40. The annuloplasty ring of claim 35, wherein the metallic core comprises concentric bands.

* * * * *